US008835498B2

(12) United States Patent
Suenobu et al.

(10) Patent No.: US 8,835,498 B2
(45) Date of Patent: Sep. 16, 2014

(54) ANTI-WRINKLE AGENTS

(75) Inventors: Noriko Suenobu, Yokohama (JP);
Chihiro Kondo, Yokohama (JP);
Takashi Yamasaki, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 120 days.

(21) Appl. No.: 13/126,714

(22) PCT Filed: Nov. 12, 2009

(86) PCT No.: PCT/JP2009/069261
§ 371 (c)(1),
(2), (4) Date: Apr. 28, 2011

(87) PCT Pub. No.: WO2010/058730
PCT Pub. Date: May 27, 2010

(65) Prior Publication Data
US 2011/0245343 A1 Oct. 6, 2011

(30) Foreign Application Priority Data
Nov. 19, 2008 (JP) .................................. 2008-294995

(51) Int. Cl.
| A61K 8/46 | (2006.01) |
| A61K 8/44 | (2006.01) |
| C07C 321/14 | (2006.01) |
| C07C 309/04 | (2006.01) |
| C07C 309/07 | (2006.01) |
| C07C 309/18 | (2006.01) |
| A61Q 19/08 | (2006.01) |
| A61K 8/42 | (2006.01) |
| A61K 31/198 | (2006.01) |

(52) U.S. Cl.
CPC .............. *A61K 31/198* (2013.01); *A61Q 19/08* (2013.01); *A61K 8/46* (2013.01); *A61K 8/466* (2013.01); *A61K 8/42* (2013.01)
USPC .............................. 514/562; 562/44; 562/426

(58) Field of Classification Search
CPC ...... A61K 8/44; C07C 321/14; C07C 309/18; A61Q 19/08
USPC ..................................... 514/562; 562/44, 426
See application file for complete search history.

(56) References Cited

U.S. PATENT DOCUMENTS

| 4,216,225 A | * | 8/1980 | Shiratsuchi et al. | .......... 514/562 |
| 4,757,066 A | | 7/1988 | Shiokari et al. | |
| 4,826,969 A | | 5/1989 | Maignan et al. | |
| 4,876,381 A | | 10/1989 | Lang et al. | |
| 4,918,223 A | | 4/1990 | Krimmer et al. | |
| 5,296,500 A | | 3/1994 | Hillebrand | |
| 6,177,089 B1 | | 1/2001 | Maignan | |
| 7,214,395 B2 | | 5/2007 | Di Pierro | |
| 7,354,610 B2 | | 4/2008 | Di Pierro | |
| 2002/0159962 A1 | | 10/2002 | Cannell et al. | |
| 2003/0229141 A1 | | 12/2003 | Yu et al. | |
| 2006/0166901 A1 | | 7/2006 | Yu et al. | |

FOREIGN PATENT DOCUMENTS

| DE | 1035855 | 8/1958 |
| EP | 0 632 038 | 1/1995 |
| JP | 33-000500 | 1/1958 |
| JP | 61-019511 | 1/1986 |
| JP | S61-233636 | 10/1986 |
| JP | 61-289016 | 12/1986 |
| JP | 62-019511 | 1/1987 |
| JP | S62-135441 | 6/1987 |
| JP | 05-032533 | 2/1993 |
| JP | 09-110627 | 4/1997 |
| JP | 11-049628 | 2/1999 |
| JP | 11-049629 | 2/1999 |
| JP | 11-080105 | 3/1999 |
| JP | 2001-192317 | 7/2001 |
| JP | 2003-137807 | 5/2003 |

(Continued)

OTHER PUBLICATIONS

Lienard, "Dynamic Combinatorial Mass Spectrometry Leads to Metallo-b-lactamase Inhibitors", J. Med. Chem. 2008, 51, 684-688.*
Isobe, "2-Chloro-1,3-dimethylimidazolinium Chloride. 2. Its Application to the Construction of Heterocycles through Dehydration Reactions", Journal of Organic Chemistry, 1999, 64, 6989-6992.*
Goodman, et al. "Potential Anticancer Agents. V. Some Sulfur-substituted Derivatives of Cysteine," *Journal of Organic Chemistry*, vol. 23, No. 9, pp. 1251-1257, Oct. 15, 1958.

(Continued)

*Primary Examiner* — Renee Claytor
*Assistant Examiner* — Sahar Javanmard
(74) *Attorney, Agent, or Firm* — Knobbe, Martens, Olson & Bear LLP

(57) ABSTRACT

Provided are anti-wrinkle agents having a novel scaffold that is suitable as components for external skin preparations such as cosmetics. The anti-wrinkle agents comprise compounds represented by general formula (1), stereoisomers thereof, or pharmacologically acceptable salts thereof. Said anti-wrinkle agents have excellent efficacy in improving wrinkles and sagging that are caused by skin aging with increased age or occur as a result of photoaging due to ultraviolet rays exposure. [In the formula, $R_1$ represents a hydrogen atom or a 1 to 8 carbon straight or branched alkyl group. $R_2$ represents $-SH$, $-SO_3H$, $-S-S-X_1$, $-S-X_2$, $-SO-X_3$, $-SO_2-X_4$, $-SO_2-NY_1-X_5$ or $-SO_2-NY_2-Y_3$. $X_1-X_5$ independently are hydrogen atoms or 1 to 8 carbon aliphatic hydrocarbon groups or 5 to 12 carbon aromatic moiety wherein carbon atoms may be substituted with heteroatoms. $Y_1$ to $Y_3$ independently represent hydrogen atoms or 1 to 8 carbon linear or branched alkyl groups. $R_3$ represents a hydrogen atom or acyl group having a 1 to 8 carbon straight or branched alkyl chain. $R_4$ represents a 5 to 12 carbon aromatic group or polycyclic condensed aromatic group that may have unsubstituted or substituted groups. m represents an integer 0-3 and n represents an integer 1 or 2].

12 Claims, 3 Drawing Sheets

(56) References Cited

FOREIGN PATENT DOCUMENTS

| | | |
|---|---|---|
| JP | 2003-267856 | 9/2003 |
| JP | 2004-533998 | 11/2004 |
| JP | 2005-089304 | 4/2005 |
| JP | 2006-052152 | 2/2006 |
| JP | 2006-327971 | 12/2006 |
| JP | 2007-191396 | 8/2007 |
| JP | 2008-105976 | 5/2008 |
| RU | 94015599 A1 | 4/1996 |
| RU | 2290921 C2 | 1/2007 |
| WO | WO 99/49856 | 10/1999 |
| WO | WO 00/39077 | 7/2000 |
| WO | WO 01/77122 | 10/2001 |
| WO | WO 01/78706 | 10/2001 |
| WO | WO 2004/024939 | 3/2004 |

OTHER PUBLICATIONS

Isobe, et al. "2-Chloro-1,3-dimethylimidazolinium Chloride. 2. Its Application to the Construction of Heterocycles through Dehydration Reactions," *Journal of Organic Chemistry*, vol. 64, No. 19, pp. 6989-6992, Aug. 24, 1999.

Plate, et al. "Conversion of Indole into 3-S-(Cysteinyl) Indoles and 2-S-(Cysteinyl) Tryptophans. An Approach to Tryptathionines," *Tetrahedron*, vol. 42, No. 16, pp. 4503-4509, 1986.

Rosowsky, et al. "Methotrexate Analogues. 32. Chain Extension, α-Carboxyl Deletion, and γ-Carboxyl Replacement by Sulfonate and Phosphonate: Effect on Enzyme Binding and Cell-growth Inhibition," *Journal of Medicinal Chemistry*, vol. 31, No. 7, pp. 1326-1331, Jan. 1, 1988.

Extended European Search Report dated Aug. 8, 2012 issued to corresponding European patent application No. 09827511.8.

Russian Office Action re Application No. 2011124914 dated Apr. 17, 2013.

Rosowsky, et al. "Side Chain Modified 5-Deazafolate and 5-Deazatetrahydrofolate Analogues as Mammalian Folypolyglutamate Synthetase and Glycinamide Ribonucleotide Formyltransferase Inhibitors: Synthesis and in Vitro Biological Evaluation," *J. Med. Chem*, vol. 35, pp. 1578-1588, 1992.

Inoue, S. "Development and Technology of Anti-aging, Whitening and Moisturing Cosmetics," C.M.C Shuppan, Publisher, Japan, Chapter 2, pp. 157-162, 2007.

International Search Report issued on Feb. 2, 2010 to international application PCT/JP2009/069261.

Decision on Grant issued in Russian Patent Application No. 2011124914, on Jul. 25, 2013.

Lerner, et al. "Ras *CAAX* Peptidomimetic FTI-277 Selectively Blocks Oncogenic Ras Signaling by Inducing Cytoplasmic Accumulation of Inactive Ras-Raf Complexes," *The Journal of Biological Chemistry*, vol. 270, No. 45, pp. 26802-26806, 1995.

\* cited by examiner

ANTI-WRINKLE AGENTS

CROSS-REFERENCE TO RELATED APPLICATIONS

This application is the U.S. National Phase under 35 U.S.C. §371 of International Application PCT/JP2009/069261, filed Nov. 12, 2009, which was published in a non-English language, which claims priority to JP Application No. 2008-294995, filed Nov. 19, 2008.

TECHNICAL FIELD

The present invention relates to a wrinkle-reducing agent and also relates to an external preparation for skin, specifically a cosmetic or the like, containing the wrinkle-reducing agent. The present invention also relates to a novel compound having a wrinkle-reducing effect.

BACKGROUND ART

Worsened skin symptoms such as wrinkles, age spots, dullness, and sagging, which are caused by factors such as increasing age, stress, and ultraviolet rays exposure, are very easily recognized by appearance as aging signs. Therefore, people have a very strong interest in skin aging phenomena, and various means have been developed for the purpose of maintaining the appearance of the skin beautifully.

Wrinkles are one of skin aging phenomena. However, at present, the mechanism of wrinkle formation has not yet been completely elucidated because the mechanism is complicated and the experimental reproduction is very difficult. Examples of the mechanism of wrinkle formation include cellular damages due to ultraviolet rays and the like and cellular apoptosis enhanced by the damages, hydrolysis of fiber components such as collagen due to increases in expression of proteases such as matrix metalloproteases (MMPs), and fiber bundle disorganization due to increased cytokines. In particular, MMPs have a variety of functions such as degrading the extracellular matrix formed of collagen, proteoglycan, elastin, and the like, and degrading proteins expressed on the surface of cells, and include a large number of subtypes. MMP1 degrades type I collagen and type III collagen as major components of the skin dermal matrix. MMP2 and MMP9 degrade type IV collagen and laminin as basement membrane components and elastin as a dermal matrix component, for example. MMP3 and MMP10 degrade proteoglycan, type IV collagen, and laminin, for example. Those degradation actions cause the decrease and degeneration of the extracellular matrix, which are recognized as one of important factors for the formation of wrinkles, sagging, and the like in the skin (see Patent Literature 1). Further, inflammatory cytokines such as TNF-α, IL-1, and IL-6 are known to be involved in the formation of wrinkles and sagging through the induction of the production of MMPs (see Patent Literature 2). As described above, those factors, which are strongly involved in skin aging phenomena such as wrinkles and sagging, are far from independent factors and also supposedly influence each other. Such situation makes the mechanism of wrinkle formation complicated.

It is widely known that retinoic acid exhibits an effect of reducing wrinkles, which are one of skin aging phenomena and occur as a result of photoaging due to irradiation with ultraviolet rays (see Non Patent Literature 1). In the United States, retinoic acid has been approved as a pharmaceutical agent for the treatment of wrinkles and acnes, and has been used as a drug for the rejuvenation of the skin in a large number of patients. In contrast, in Japan, retinoic acid has not been approved because of its problems in terms of safety such as irritation to the skin. Further, some attempts have been made on reducing wrinkles using a blend of collagen and hyaluronic acid (see Patent Literatures 3 and 4), and besides, ascorbic acid (see Patent Literature 5), tocopherol (see Patent Literature 6), or the like is known as the wrinkle-reducing agent. However, no wrinkle-reducing material that gives sufficiently satisfactory results has been found for, for example, the following reasons: the wrinkle-reducing agent does not have any sufficient wrinkle-reducing effect; and the wrinkle-reducing agent may cause problems in terms of safety or stability such as expression of an undesired drug effect at a concentration at which a wrinkle-reducing effect is expressed. Thus, there has been a strong demand for the development of a novel wrinkle-reducing agent.

With regard to amino acids, there are a large number of amino acids including naturally-occurring and non-naturally-occurring amino acids. Those amino acids are known to serve as functional polymers responsible for the maintenance of biological structures and biological reactions, and besides, to exhibit various bioactivities. The naturally-occurring amino acids or derivatives thereof are expected to have not only bioactivities but also high safety, and are thus widely employed in the fields of foods, cosmetics, and pharmaceutical agents, for example. In particular, in the field of cosmetics, it is known that alanine exhibits a skin-whitening action (see Patent Literature 7), an α-amino acid derivative exhibits a parakeratosis inhibitory action, a pore-shrinking action, or a rough skin-preventing/ameliorating action (see Patent Literature 8), a cysteic acid or homocysteic acid exhibits a skin desquamation-promoting or epidermal renewal-stimulating action (see Patent Literature 9), an N-acyl amino acid exhibits a hair growth-promoting action and a moisture-retaining action (see Patent Literature 10), and an essential amino acid such as glutamine exhibits a cell-stimulatory action (see Patent Literature 11). Further, alanine is known to have a wrinkle-reducing action (see Patent Literature 12).

CITATION LIST

Patent Literature

[PTL 1] JP 2001-192317 A
[PTL 2] JP 2005-089304 A
[PTL 3] JP 33-500 A
[PTL 4] JP 2007-191396 A
[PTL 5] JP 2003-267856 A
[PTL 6] JP 62-19511 A
[PTL 7] JP 11-049629 A
[PTL 8] JP 2006-327971 A
[PTL 9] JP 09-110627 A
[PTL 10] JP 11-080105 A
[PTL 11] JP 61-289016 A
[PTL 12] JP 11-49628 A

Non-Patent Literature

[NPL 1] Development technology for anti-aging, whitening, and moisture-retaining cosmetics, CMC Publishing Co., Ltd., Masato Suzuki (ed.)

SUMMARY OF INVENTION

Technical Problem

The present invention has been made in view of the above-mentioned circumstances. An object of the present invention is to provide a wrinkle-reducing agent that is suitable for an ingredient for an external preparation for skin and has a novel scaffold.

Solution to Problem

The inventors of the present invention have made extensive studies to seek a novel scaffold having a wrinkle-reducing action. As a result, the inventors have found that a compound represented by the following general formula (1), a stereoisomer of the compound, and a pharmacologically acceptable salt thereof have excellent wrinkle-reducing effects on wrinkles formed by ultraviolet rays exposure and the like. Thus, the present invention has been completed.

That is, the present invention is as follows.

<1> A wrinkle-reducing agent, including a compound represented by the following general formula (1), a stereoisomer of the compound, or a pharmacologically acceptable salt thereof.

[Chem. 1]

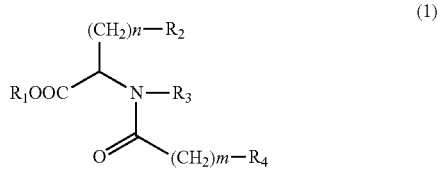

(1)

[In the formula, $R_1$ represents a hydrogen atom or a linear or branched alkyl group having 1 to 8 carbon atoms; $R_2$ represents —SH, —$SO_3H$, —S—$X_1$, —S—$X_2$, —SO—$X_3$, —$SO_2$—$X_4$, —$SO_2$—$NY_1$—$X_5$, or —$SO_2$—$NY_2$—$Y_3$, provided that the $X_1$ to $X_5$ each independently represent an aliphatic hydrocarbon group having 1 to 8 carbon atoms or an aromatic moiety having 5 to 12 carbon atoms, in which a heteroatom may be substituted for a hydrogen atom or a carbon atom, and the $Y_1$ to $Y_3$ each independently represent a hydrogen atom or a linear or branched alkyl group having 1 to 8 carbon atoms; $R_3$ represents a hydrogen atom or an acyl group having a linear or branched alkyl chain having 1 to 8 carbon atoms; $R_4$ represents an optionally unsubstituted or substituted aromatic group or polycyclic condensed aromatic group having 5 to 12 carbon atoms; m represents an integer of 0 to 3; and n represents an integer of 1 or 2.]

<2> The wrinkle-reducing agent according to Item <1>, in which the compound represented by the general formula (1) is a compound represented by the following general formula (2).

[Chem. 2]

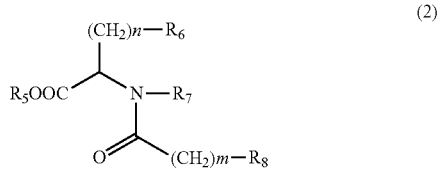

(2)

[In the formula, $R_5$ represents a hydrogen atom or a linear or branched alkyl group having 1 to 8 carbon atoms; $R_6$ represents —S—$X_2$, provided that the $X_2$ represents an aliphatic hydrocarbon group having 1 to 8 carbon atoms or an aromatic moiety having 5 to 12 carbon atoms, in which a heteroatom may be substituted for a hydrogen atom or a carbon atom; $R_7$ represents a hydrogen atom or an acyl group having a linear or branched alkyl chain having 1 to 8 carbon atoms; $R_8$ represents an optionally unsubstituted or substituted aromatic group or polycyclic condensed aromatic group having 5 to 12 carbon atoms; m represents an integer of 0 to 3; and n represents an integer of 1 or 2.]

<3> The wrinkle-reducing agent according to Item <1>, in which the compound represented by the general formula (1) is a compound represented by the following general formula (3).

[Chem. 3]

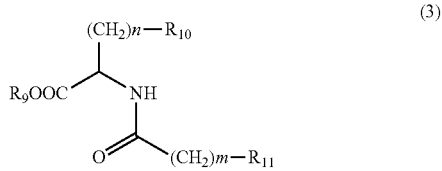

(3)

[In the formula, $R_9$ represents a hydrogen atom or a linear or branched alkyl group having 1 to 8 carbon atoms; $R_{10}$ represents —S—$X_2$, provided that the $X_2$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{11}$ represents an optionally unsubstituted or substituted aromatic group or polycyclic condensed aromatic group having 5 to 12 carbon atoms; m represents an integer of 0 to 3; and n represents an integer of 1 or 2.]

<4> The wrinkle-reducing agent according to Item <1>, in which the compound represented by the general formula (1) is a compound represented by the following general formula (4).

[Chem. 4]

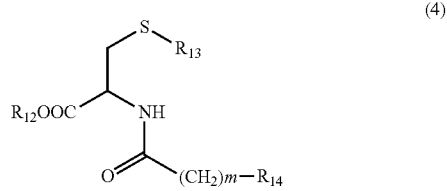

(4)

[In the formula, $R_{12}$ represents a hydrogen atom or a linear or branched alkyl group having 1 to 8 carbon atoms; $R_{13}$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{14}$ represents an optionally unsubstituted or substituted aromatic group or polycyclic condensed aromatic group having 5 to 12 carbon atoms; and m represents an integer of 0 to 3.]

<5> The wrinkle-reducing agent according to Item <1>, in which the compound represented by the general formula (1) is a compound represented by the following general formula (5).

[Chem. 5]

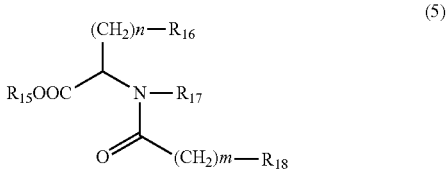

(5)

[In the formula, $R_{15}$ represents a hydrogen atom or a linear or branched alkyl group having 1 to 8 carbon atoms; $R_{16}$ represents —$SO_3H$ or —$SO_2$—$X_4$, provided that the $X_4$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{17}$ represents a hydrogen atom or an acyl group having a linear or branched alkyl chain having 1 to 8 carbon atoms; $R_{18}$ represents an optionally unsubstituted or substituted aromatic group or polycyclic condensed aromatic group having 5 to 12 carbon atoms; m represents an integer of 0 to 3; and n represents an integer of 1 or 2.]

<6> The wrinkle-reducing agent according to Item <1>, in which the compound represented by the general formula (1) is a compound represented by the following general formula (6).

[Chem. 6]

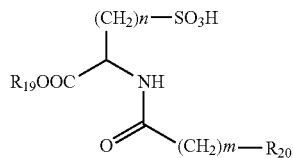

(6)

[In the formula, $R_{19}$ represents a hydrogen atom or a linear or branched alkyl group having 1 to 8 carbon atoms; $R_{20}$ represents an optionally unsubstituted or substituted aromatic group or polycyclic condensed aromatic group having 5 to 12 carbon atoms; m represents an integer of 0 to 3; and n represents an integer of 1 or 2.]

<7> A compound, which is represented by the following general formula (5), a stereoisomer of the compound, or a pharmacologically acceptable salt thereof.

[Chem. 7]

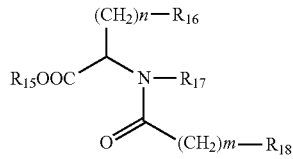

(5)

[In the formula, $R_{15}$ represents a hydrogen atom or a linear or branched alkyl group having 1 to 8 carbon atoms; $R_{16}$ represents —$SO_3H$ or —$SO_2$—$X_4$, provided that the $X_4$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{17}$ represents a hydrogen atom or an acyl group having a linear or branched alkyl chain having 1 to 8 carbon atoms; $R_{18}$ represents an optionally unsubstituted or substituted aromatic group or polycyclic condensed aromatic group having 5 to 12 carbon atoms; m represents an integer of 0 to 3; and n represents an integer of 1 or 2.]

<8> A compound, which is represented by the following general formula (6), a stereoisomer of the compound, or a pharmacologically acceptable salt thereof.

[Chem. 8]

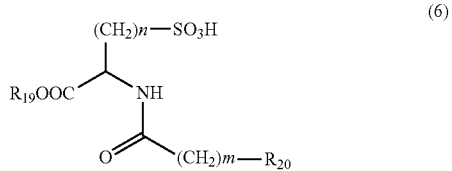

(6)

[In the formula, $R_{19}$ represents a hydrogen atom or a linear or branched alkyl group having 1 to 8 carbon atoms; $R_{20}$ represents an optionally unsubstituted or substituted aromatic group or polycyclic condensed aromatic group having 5 to 12 carbon atoms; m represents an integer of 0 to 3; and n represents an integer of 1 or 2.]

<9> An external preparation for skin, including the wrinkle-reducing agent according to any one of Items <1> to <6> in an amount of 0.001 to 20% by mass.

<10> The external preparation for skin according to Item <9>, in which the external preparation for skin is a cosmetic use.

<11> A wrinkle-reducing method, including administering, to a site needed for reducing wrinkles, the compound represented by the following general formula (1), a stereoisomer of the compound, or a pharmacologically acceptable salt thereof.

[Chem. 9]

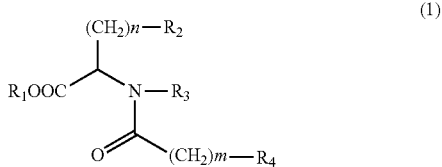

(1)

[In the formula, $R_1$ represents a hydrogen atom or a linear or branched alkyl group having 1 to 8 carbon atoms; $R_2$ represents —SH, —$SO_3H$, —S—S—$X_1$, —S—$X_2$, —$SO_2$—$X_4$, —$SO_2$—$NY_1$—$X_5$, or —$SO_2$—$NY_2$—$Y_3$, provided that the $X_1$ to $X_5$ each independently represent an aliphatic hydrocarbon group having 1 to 8 carbon atoms or an aromatic moiety having 5 to 12 carbon atoms, in which a heteroatom may be substituted for a hydrogen atom or a carbon atom, and the $Y_1$ to $Y_3$ each independently represent a hydrogen atom or a linear or branched alkyl group having 1 to 8 carbon atoms; $R_3$ represents a hydrogen atom or an acyl group having a linear or branched alkyl chain having 1 to 8 carbon atoms; $R_4$ represents an optionally unsubstituted or substituted aromatic group or polycyclic condensed aromatic group having 5 to 12 carbon atoms; m represents an integer of 0 to 3; and n represents an integer of 1 or 2.]

Advantageous Effects of Invention

According to the present invention, the novel wrinkle-reducing agent can be provided. Further, the external preparation for skin and cosmetic each containing the novel wrinkle-reducing agent can be provided. Further, the novel compound having a wrinkle-reducing action can be provided.

Figure 1:
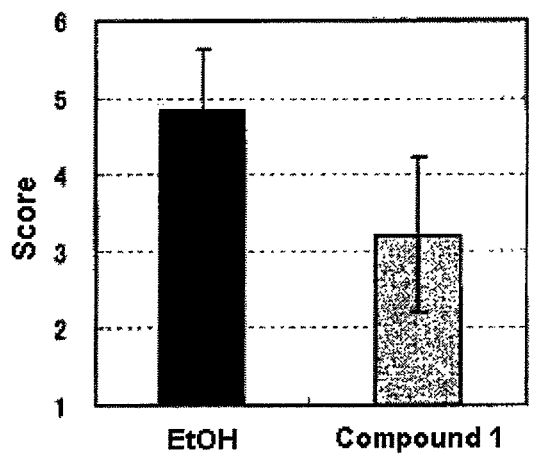
FIG. 1 is a graph illustrating a wrinkle-reducing action of Compound 1 in the present invention using a photoaging model.

DESCRIPTION OF EMBODIMENTS (1) Compound Represented by General Formula (1) Contained in Wrinkle-Reducing Agent of Present Invention An active ingredient of the wrinkle-reducing agent of the present invention is a compound represented by the following general formula (1), a stereoisomer of the compound, or a pharmacologically acceptable salt thereof.

[Chem. 10]

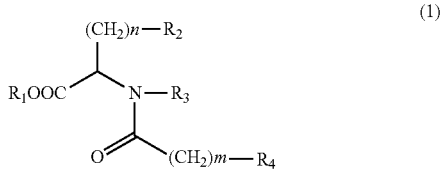

(1)

In the general formula (1), $R_1$ represents a hydrogen atom or a linear or branched alkyl group having 1 to 8 carbon atoms; $R_2$ represents —SH, —SO$_3$H, —S—S—X$_1$, —S—X$_2$, —SO—X$_3$, —SO$_2$—X$_4$, —SO$_2$—NY$_1$—X$_5$, or —SO$_2$—NY$_2$—Y$_3$, provided that the $X_1$ to $X_5$ each independently represent an aliphatic hydrocarbon group having 1 to 8 carbon atoms or an aromatic moiety having 5 to 12 carbon atoms, in which a heteroatom may be substituted for a hydrogen atom or a carbon atom, and the $Y_1$ to $Y_3$ each independently represent a hydrogen atom or a linear or branched alkyl group having 1 to 8 carbon atoms; $R_3$ represents a hydrogen atom or an acyl group having a linear or branched alkyl chain having 1 to 8 carbon atoms; $R_4$ represents an optionally unsubstituted or substituted aromatic group or polycyclic condensed aromatic group having 5 to 12 carbon atoms; m represents an integer of 0 to 3; and n represents an integer of 1 or 2. Here, the above-mentioned aromatic moiety includes an aromatic hydrocarbon group such as a toluyl group, a xylyl group, a benzyl group, or a naphthylmethyl group as well as an aromatic group such as a phenyl group, a pyridyl group, a naphthyl group, or a biphenyl group.

Suitable examples of such compound represented by the general formula (1) include a compound represented by the general formula (2) as described later and a compound represented by the general formula (5) as described later. The compound represented by the general formula (2) is more preferably a compound represented by the general formula (3), still more preferably a compound represented by the general formula (4). Further, the compound represented by the general formula (5) is more preferably a compound represented by the general formula (6). In a compound in which $R_2$ represents a thiol group out of the compounds represented by the general formula (1), thiol moieties are linked via a disulfide bond to form a dimer. Such dimer is also included in the general formula (1) of the present invention. It goes without saying that a wrinkle-reducing agent containing a compound that is included in the general formula (1) and is not included in any of the compound represented by the general formula (2) and the compound represented by the general formula (5) is also the wrinkle-reducing agent of the present invention.

Specific examples of each of $Y_1$ to $Y_3$ in $R_1$ and $R_2$ include a hydrogen atom, a methyl group, an ethyl group, a propyl group, a butyl group, a pentyl group, a hexyl group, a heptyl group, and an octyl group. Of those, a linear or branched alkyl group having 1 to 4 carbon atoms is preferred and a hydrogen atom, a methyl group, and an ethyl group are more preferred.

Specific examples of each of $X_1$ to $X_6$ in $R_2$ include a methyl group, an ethyl group, a propyl group, a butyl group, a pentyl group, a hexyl group, a heptyl group, an octyl group, a phenyl group, a toluyl group, a benzyl group, a phenethyl group, a phenylpropyl group, apyridyl group, a quinolyl group, a naphthyl group, abiphenyl group, a 2-hydroxyethyl group, a 2-hydroxypropyl group, a 3-hydroxypropyl group, and a 2,3-dihydroxypropyl group.

$R_2$ preferably represents —SO$_3$H, —S—X$_2$, or —SO$_2$—X$_4$.

Specific examples of $R_3$ include a hydrogen atom, an acetyl group, a propionyl group, a butyryl group, an isobutyryl group, a valeryl group, an isovaleryl group, a pivaloyl group, a hexanoyl group, and an octanoyl group. Of those, a hydrogen atom, an acetyl group, and a propionyl group are preferred.

Specific examples of $R_4$ include a phenyl group, a toluyl group, an ethylphenyl group, a propylphenyl group, a butylphenyl group, a pentylphenyl group, a hexylphenyl group, a methoxyphenyl group, an ethoxyphenyl group, a propyloxyphenyl group, a butyloxyphenyl group, a pentyloxyphenyl group, a hexyloxyphenyl group, a hydroxyphenyl group, an aminophenyl group, a fluorophenyl group, a trifluoromethylphenyl group, a chlorophenyl group, a dichlorophenyl group, a nitrophenyl group, a cyanophenyl group, an (N-methylamino)phenyl group, an (N-ethylamino)phenyl group, an (N-propylamino)phenyl group, an (N-butylamino) phenyl group, an N,N-(dimethylamino)phenyl group, an N,N-(diethylamino)phenyl group, an N,N-(dipropylamino) phenyl group, an N,N-(dibutylamino)phenyl group, an acetylphenyl group, a propionylphenyl group, an butyrylphenyl group, a carboxylphenyl group, a methoxycarbonylphenyl group, an ethoxycarbonylphenyl group, a propyloxycarbonylphenyl group, a naphthyl group, a methylnaphthyl group, a methoxynaphthyl group, a hydroxynaphthyl group, an aminonaphthyl group, a fluoronaphthyl group, a trifluoromethylnaphthyl group, an acetylnaphthyl group, a carboxynaphthyl group, a methoxycarbonylnaphthyl group, an ethoxycarbonylnaphthyl group, a biphenyl group, a pyridyl group, and a quinolyl group. Of those, a phenyl group, a toluyl group, an ethylphenyl group, a propylphenyl group, a methoxyphenyl group, an ethoxyphenyl group, a fluorophenyl group, a trifluorophenyl group, a naphthyl group, a biphenyl group, and the like are preferred.

The compound represented by the general formula (1) may be manufactured by a method as described later. Such compound exhibits, for example, excellent potency for the wrinkle-reducing effect of the compound and/or skin penetration profile of the compound. As a result, the compound has an advantage in terms of having an excellent wrinkle-reducing effect on wrinkles formed by ultraviolet rays exposure and the like. Further, the compound is low in skin irritation property, sensitizing property, and the like, and hence has extremely high safety to the skin. In addition, the compound is highly soluble in not only a non-polar solvent but also a polar solvent, and hence, there is no or extremely low risk that the blending amount of the compound itself is restricted. Those compounds have procollagen production-promoting actions and express wrinkle-reducing effects. In addition, the wrinkle-reducing effects are also estimated to be expressed through the above-mentioned inhibiting actions on MMPs or IL-1 or IL-6.

Out of the compounds represented by the general formula (1), the compounds represented by the following general formula (2), (3), and (4) are described.

[Chem. 11]

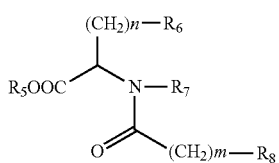

(2)

In the general formula (2), $R_5$ represents a hydrogen atom or a linear or branched alkyl group having 1 to 8 carbon atoms; $R_6$ represents —S—$X_2$, provided that the $X_2$ represents an aliphatic hydrocarbon group having 1 to 8 carbon atoms or an aromatic moiety having 5 to 12 carbon atoms, in which a heteroatom may be substituted for a hydrogen atom or a carbon atom; $R_7$ represents a hydrogen atom or an acyl group having a linear or branched alkyl chain having 1 to 8 carbon atoms; $R_8$ represents an optionally unsubstituted or substituted aromatic group or polycyclic condensed aromatic group having 5 to 12 carbon atoms; m represents an integer of 0 to 3; and n represents an integer of 1 or 2.

[Chem. 12]

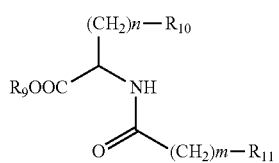

(3)

In the general formula (3), $R_9$ represents a hydrogen atom or a linear or branched alkyl group having 1 to 8 carbon atoms; $R_{10}$ represents —S—$X_2$, provided that the $X_2$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{11}$ represents an optionally unsubstituted or substituted aromatic group or polycyclic condensed aromatic group having 5 to 12 carbon atoms; m represents an integer of 0 to 3; and n represents an integer of 1 or 2.

[Chem. 13]

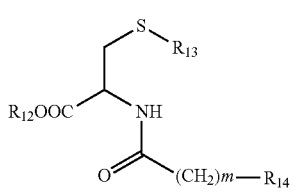

(4)

In the general formula (4), $R_{12}$ represents a hydrogen atom or a linear or branched alkyl group having 1 to 8 carbon atoms; $R_{13}$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{14}$ represents an optionally unsubstituted or substituted aromatic group or polycyclic condensed aromatic group having 5 to 12 carbon atoms; and m represents an integer of 0 to 3.

As described above, the general formula (2) is a preferred form of the general formula (1), the general formula (3) is a more preferred form of the general formula (1), and the general formula (4) is a still more preferred form of the general formula (1).

Specific examples of the compound represented by the general formula (4) include (N-benzoyl)cysteine, (N-toluyl)cysteine, (N-methoxybenzoyl)cysteine, (N-biphenylcarbonyl)cysteine, (N-benzylcarbonyl)cysteine, (N-benzoyl-S-methyl)cysteine, (S-methyl-N-toluyl)cysteine, [N-(ethylbenzoyl)-S-methyl]cysteine, [S-methyl-N-(propylbenzoyl)]cysteine, [N-(butylbenzoyl)-S-methyl]cysteine, [N-(methoxybenzoyl)-S-methyl]cysteine, [N-(ethoxybenzoyl)-S-methyl]cysteine, [N-(propyloxybenzoyl)-S-methyl]cysteine, [N-(butyloxybenzoyl)-S-methyl]cysteine, [N-(hydroxybenzoyl)-S-methyl]cysteine, [N-(aminobenzoyl)-S-methyl]cysteine, [N—(N'-methylaminobenzoyl)-S-methyl]cysteine, [N—(N'-ethylaminobenzoyl)-S-methyl]cysteine, [N—(N',N'-dimethylaminobenzoyl)-S-methyl]cysteine, [N—(N',N'-diethylaminobenzoyl)-S-methyl]cysteine, [N-(fluorobenzoyl)-S-methyl]cysteine, [N-(trifluoromethylbenzoyl)-S-methyl]cysteine, [N-(chlorobenzoyl)-S-methyl]cysteine, [N-(dichlorobenzoyl)-S-methyl]cysteine, [N-(nitrobenzoyl)-S-methyl]cysteine, [(N-cyanobenzoyl)-S-methyl]cysteine, [N-(carboxybenzoyl)-S-methyl]cysteine, [N-(methoxycarbonylbenzoyl)-S-methyl]cysteine, [N-(ethoxycarbonylbenzoyl)-S-methyl]cysteine, [N-(acetylbenzoyl)-S-methyl]cysteine, [S-methyl-N-(propionylbenzoyl)]cysteine, [N-(butyrylbenzoyl)-S-methyl]cysteine, [N-(naphthoyl)-S-methyl]cysteine, [N-(methylnaphthoyl)-S-methyl]cysteine, [N-(methoxynaphthoyl)-S-methyl]cysteine, [N-(hydroxynaphthoyl)-S-methyl]cysteine, [N-(aminonaphthoyl)-S-methyl]cysteine, [N-(acetylnaphthoyl)-S-methyl]cysteine, [N-(fluoronaphthoyl)-S-methyl]cysteine, [N-(methoxycarbonylnaphthoyl)-S-methyl]cysteine, [N-(biphenylcarbonyl)-S-methyl]cysteine, [N-(methoxybiphenylcarbonyl)-S-methyl]cysteine, [N-(benzylcarbonyl)-S-methyl]cysteine, [N-(phenylethylcarbonyl)-S-methyl]cysteine, [N-(phenylpropylcarbonyl)-S-methyl]cysteine, [N-(toluyl)methylcarbonyl]cysteine, [N-(toluylethylcarbonyl)-S-methyl]cysteine, [N-(toluylpropylcarbonyl]-S-methyl]cysteine, [S-methyl-N-(pyridylcarbonyl)]cysteine, [S-methyl-N-(quinolylcarbonyl)]cysteine, [(N-benzoyl-S-methyl)cysteine]methyl ester, [(N-benzoyl-S-methyl)cysteine]ethyl ester, [(N-benzoyl-S-methyl)cysteine]propyl ester, [(S-methyl-N-toluyl)cysteine]methyl ester, [(S-methyl-N-toluyl)cysteine]ethyl ester, [(S-methyl-N-toluyl)cysteine]propyl ester, [S-methyl-N-(methoxybenzoyl)cysteine]methyl ester, [S-methyl-N-(methoxybenzoyl)cysteine]ethyl ester, [S-methyl-N-(methoxybenzoyl)cysteine]propyl ester, [N-(biphenylcarbonyl)-S-methyl cysteine]methyl ester, [N-(biphenylcarbonyl)-S-methyl cysteine]ethyl ester, [[N-(biphenylcarbonyl)-S-methyl]cysteine]propyl ester, [[N-(benzylcarbonyl)-S-methyl]cysteine]methyl ester, [[N-(benzylcarbonyl)-S-methyl]cysteine]ethyl ester, [[N-(benzylcarbonyl)-S-methyl]cysteine]propyl ester, (N-benzoyl-S-ethyl)cysteine, (N-benzoyl-S-propyl)cysteine, (N-benzoyl-S-butyl)cysteine, (N-benzoyl-S-phenyl)cysteine, (N-benzoyl-S-benzyl)cysteine, (N-benzoyl-S-phenylethyl)cysteine, (N-benzoyl-S-pyridyl)cysteine, (N-benzoyl-S-quinolyl)cysteine, (N-benzoyl-S-naphthyl)cysteine, (N-benzyl-S-biphenyl)cysteine, (S-ethyl-N-toluyl)cysteine, (S-propyl-N-toluyl)cysteine, (S-butyl-N-toluyl)cysteine, (S-phenyl-N-toluyl)cysteine, (S-benzyl-N-toluyl)cysteine, (S-phenylethyl-N-toluyl)cysteine, (S-pyridyl-N-toluyl)cysteine, (S-quinolyl-N-toluyl)cysteine, (S-naphthyl-N-toluyl)cysteine, (N-toluyl-S-biphenyl)cysteine, (S-ethyl-N-methoxybenzoyl)cysteine, (N-methoxybenzoyl-S-propyl)cysteine, (S-butyl-N-methoxybenzoyl)cysteine, (N-methoxybenzoyl-S-phenyl)cysteine, (S-benzyl-N-methoxybenzoyl)cysteine, (N-methoxybenzoyl-S-phenylethyl)cysteine, (N-methoxybenzoyl-S-pyridyl)cysteine, (N-methoxybenzoyl-S-quinolyl)cysteine, (N-methoxybenzoyl-S-naphthyl)cysteine, (S-biphenyl-N-methoxybenzyl)cysteine, (N-biphenylcarbonyl-S-ethyl)cysteine, (N-biphenylcarbonyl-S-propyl)cysteine, (N-biphenylcarbonyl-S-butyl)cysteine, (N-biphenylcarbonyl-S-phenyl)cysteine, (N-biphenylcarbonyl-S-benzyl)cysteine, (N-biphenylcarbonyl-S-phenylethyl)cysteine, (N-biphenylcarbonyl-S-pyridyl)cysteine, (N-biphenylcarbonyl-S-quinolyl)cysteine, (N-biphenylcarbonyl-S-naphthyl)cysteine, (N-biphenylcarbonyl-S-biphenyl)cysteine, (N-benzylcarbonyl-S-ethyl)cysteine, (N-benzylcarbonyl-S-propyl)cysteine, (N-benzylcarbonyl-S-butyl)cysteine, (N-benzylcarbonyl-S-phenyl)cysteine, (N-benzylcarbonyl-S-benzyl)cysteine, (N-benzylcarbonyl-S-phenylethyl)cysteine, (N-benzylcarbonyl-S-pyridyl)cysteine, (N-benzylcarbonyl-S-quinolyl)cysteine, (N-benzylcarbonyl-S-naphthyl)cysteine, (N-benzylcarbonyl-S-biphenyl)cysteine, [(S-ethyl-N-toluyl)cysteine]methyl ester, [(S-propyl-N-toluyl)cysteine]methyl ester, [(S-butyl-N-toluyl)cysteine]methyl ester, [(S-phenyl-N-toluyl)cysteine]methyl ester, [(S-benzyl-N-toluyl)cysteine]methyl ester, [(S-phenylethyl-N-toluyl)cysteine]methyl ester, [(S-pyridyl-N-toluyl)cysteine]methyl ester, [(S-quinolyl-N-toluyl)cysteine]methyl ester, [(S-naphthyl-N-toluyl)cysteine]methyl ester, [(N-toluyl-S-biphenyl)cysteine]methyl ester, [(S-ethyl-N-methoxybenzoyl)cysteine]methyl ester, [(N-methoxybenzoyl-S-propyl)cysteine]methyl ester, [(S-butyl-N-methoxybenzoyl)cysteine]methyl ester, [(N-methoxybenzoyl-S-phenyl)cysteine]methyl ester, [(S-benzyl-N-methoxybenzoyl)cysteine]methyl ester, [(N-methoxybenzoyl-S-phenylethyl)cysteine]methyl ester, [(N-methoxybenzoyl-S-pyridyl)cysteine]methyl ester, [(N-methoxybenzoyl-S-quinolyl)cysteine]methyl ester, [(N-methoxybenzoyl-S-naphthyl)cysteine]methyl ester, [(S-biphenyl-N-methoxybenzyl)cysteine]methyl ester, [(N-biphenylcarbonyl-S-ethyl)cysteine]methyl ester, [(N-biphenylcarbonyl-S-propyl)cysteine]methyl ester, [(N-biphenylcarbonyl-S-butyl)cysteine]methyl ester, [(N-biphenylcarbonyl-S-phenyl)cysteine]methyl ester, [(N-biphenylcarbonyl-S-benzyl)cysteine]methyl ester, [(N-biphenylcarbonyl-S-phenylethyl)cysteine]methyl ester, [(N-biphenylcarbonyl-S-pyridyl)cysteine]methyl ester, [(N-biphenylcarbonyl-S-quinolyl)cysteine]methyl ester, [(N-biphenylcarbonyl-S-naphthyl)cysteine]methyl ester, [(N-biphenylcarbonyl-S-biphenyl)cysteine]methyl ester, [(N-benzylcarbonyl-S-ethyl)cysteine]methyl ester, [(N-benzylcarbonyl-S-propyl)cysteine]methyl ester, [(N-benzylcarbonyl-S-butyl)cysteine]methyl ester, [(N-benzylcarbonyl-S-phenyl)cysteine]methyl ester, [(N-benzylcarbonyl-S-benzyl)cysteine]methyl ester, [(N-benzylcarbonyl-S-phenylethyl)cysteine]methyl ester, [(N-benzylcarbonyl-S-pyridyl)cysteine]methyl ester, [(N-benzylcarbonyl-S-quinolyl)cysteine]methyl ester, [(N-benzylcarbonyl-S-naphthyl)cysteine]methyl ester, [(N-benzylcarbonyl-S-biphenyl)cysteine]methyl ester, (N-benzoyl)homocysteine, (N-toluyl)homocysteine, (N-methoxybenzoyl)homocysteine, (N-biphenylcarbonyl)homocysteine, (N-benzylcarbonyl)homocysteine, (N-benzoyl)methionine, [N-(toluyl)]methionine, [N-(ethylbenzoyl)]methionine, [N-(propylbenzoyl)]methionine, [N-(butylbenzoyl)]methionine, [N-(methoxybenzoyl)]methionine, [N-(ethoxybenzoyl)]methionine, [N-(propyloxybenzoyl)]methionine, [N-(butyloxybenzoyl)]methionine, [N-(hydroxybenzoyl)]methionine, [N-(aminobenzoyl)]methionine, [N—(N'-methylaminobenzoyl)]methionine, [N—(N'-ethylaminobenzoyl)]methionine, [N—(N',N'-dimethylaminobenzoyl)]methionine, [N—(N',N'-diethylaminobenzoyl)]methionine, [N-(fluorobenzoyl)]methionine, [N-(trifluoromethylbenzoyl)]methionine, [N-(chlorobenzoyl)]methionine, [N-(dichlorobenzoyl)]methionine, [N-(nitrobenzoyl)]methionine, [(N-cyanobenzoyl)]methionine, [N-(carboxybenzoyl)]methionine, [N-(methoxycarbonylbenzoyl)]methionine, [N-(ethoxycarbonylbenzoyl)]methionine, [N-(acetylbenzoyl)]methionine, [N-(propionylbenzoyl)]methionine, [N-(butyrylbenzoyl)]methionine, [N-(naphthoyl)]methionine, [N-(methylnaphthoyl)]methionine, [N-(methoxynaphthoyl)]methionine, [N-(hydroxynaphthoyl)]methionine, [N-(aminonaphthoyl)]methionine, [N-(acetylnaphthoyl)]methionine, [N-(fluoronaphthoyl)]methionine, [N-(carboxynaphthoyl)]methionine, [N-(methoxycarbonylnaphthoxy)]methionine, [N-(biphenylcarbonyl)]methionine, [N-(methoxybiphenylcarbonyl)]methionine, N-(benzylcarbonyl)methionine, N-(phenylethylcarbonyl)methionine, N-(phenylpropylcarbonyl)methionine, [N-(toluylmethyl)carbonyl]methionine, [N-(toluylethyl)carbonyl]methionine, [N-(toluylpropyl)carbonyl]methionine, N-(pyridylcarbonyl)methionine, N-(quinolylcarbonyl)methionine, [(N-benzoyl)methionine]methyl ester, [(N-benzoyl)methionine]ethyl ester, [(N-benzoyl)methionine]propyl ester, [(N-toluyl)methionine]methyl ester, [(N-toluyl)methionine]ethyl ester, [(N-toluyl)methionine]propyl ester, [N-(methoxybenzoyl)methionine]methyl ester, [N-(methoxybenzoyl)methionine]ethyl ester, [N-(methoxybenzoyl)methionine]propyl ester, [N-(biphenylcarbonyl)methionine]methyl ester, [N-(biphenylcarbonyl)methionine]ethyl ester, [N-(biphenylcarbonyl)methionine]propyl ester, [N-(benzylcarbonyl)methionine]methyl ester, [N-(benzylcarbonyl)methionine]ethyl ester, [N-(benzylcarbonyl)methionine]propyl ester, stereoisomers of the compounds described above, or pharmacologically acceptable salts thereof. Of those, more preferred are N-(benzoyl)cysteine, N-(toluyl)cysteine, N-(methoxybenzoyl)cysteine, N-(biphenylcarbonyl)cysteine, N-(benzylcarbonyl)cysteine, [N-(benzoyl)-S-methyl]cysteine, [N-(toluyl)-S-methyl]cysteine, [N-(methoxybenzoyl)-S-methyl]cysteine, [N-(biphenylcarbonyl)-S-methyl]cysteine, [N-(benzylcarbonyl)-S-methyl]cysteine, [N-(benzoyl)cysteine]methyl ester, [N-(toluyl)cysteine]methyl ester, [N-(methoxybenzoyl)cysteine]methyl ester, [N-(biphenylcarbonyl)cysteine]methyl ester, [N-(benzylcarbonyl)cysteine]methyl ester, (N-benzoyl)methionine, [N-(toluyl)]methionine, stereoisomers of the compounds, or pharmacologically acceptable salts thereof.

Of the compounds represented by the general formula (3), specific examples of the compounds which are not included in the general formula (4) include (N-benzoyl-S-ethyl)homocysteine, (N-benzoyl-S-propyl)homocysteine, (N-benzoyl-S-butyl)homocysteine, (N-benzoyl-S-phenyl)homocysteine, (N-benzoyl-S-benzyl)homocysteine, (N-benzoyl-S-phenylethyl)homocysteine, (N-benzoyl-S-pyridyl)

homocysteine, (N-benzoyl-S-quinolyl)homocysteine, (N-benzoyl-S-naphthyl)homocysteine, (N-benzyl-S-biphenyl)homocysteine, (S-ethyl-N-toluyl)homocysteine, (S-propyl-N-toluyl)homocysteine, (S-butyl-N-toluyl)homocysteine, (S-phenyl-N-toluyl)homocysteine, (S-benzyl-N-toluyl)homocysteine, (S-phenylethyl-N-toluyl)homocysteine, (S-pyridyl-N-toluyl)homocysteine, (S-quinolyl-N-toluyl)homocysteine, (S-naphthyl-N-toluyl)homocysteine, (N-toluyl-S-biphenyl)homocysteine, (S-ethyl-N-methoxybenzoyl)homocysteine, (N-methoxybenzoyl-S-propyl)homocysteine, (S-butyl-N-methoxybenzoyl)homocysteine, (N-methoxybenzoyl-S-phenyl)homocysteine, (S-benzyl-N-methoxybenzoyl)homocysteine, (N-methoxybenzoyl-S-phenylethyl)homocysteine, (N-methoxybenzoyl-S-pyridyl)homocysteine, (N-methoxybenzoyl-S-quinolyl)homocysteine, (N-methoxybenzoyl-S-naphthyl)homocysteine, (S-biphenyl-N-methoxybenzyl)homocysteine, (N-biphenylcarbonyl-S-ethyl)homocysteine, (N-biphenylcarbonyl-S-propyl)homocysteine, (N-biphenylcarbonyl-S-butyl)homocysteine, (N-biphenylcarbonyl-S-phenyl)homocysteine, (N-biphenylcarbonyl-S-benzyl)homocysteine, (N-biphenylcarbonyl-S-phenylethyl)homocysteine, (N-biphenylcarbonyl-S-pyridyl)homocysteine, (N-biphenylcarbonyl-S-quinolyl)homocysteine, (N-biphenylcarbonyl-S-naphthyl)homocysteine, (N-biphenylcarbonyl-S-biphenyl)homocysteine, (N-benzylcarbonyl-S-ethyl)homocysteine, (N-benzylcarbonyl-S-propyl)homocysteine, (N-benzylcarbonyl-S-butyl)homocysteine, (N-benzylcarbonyl-S-phenyl)homocysteine, (N-benzylcarbonyl-S-benzyl)homocysteine, (N-benzylcarbonyl-S-phenylethyl)homocysteine, (N-benzylcarbonyl-S-pyridyl)homocysteine, (N-benzylcarbonyl-S-quinolyl)homocysteine, (N-benzylcarbonyl-S-naphthyl)homocysteine, (N-benzylcarbonyl-S-biphenyl)homocysteine, [(S-ethyl-N-toluyl)homocysteine]methyl ester, [(S-propyl-N-toluyl)homocysteine]methyl ester, [(S-butyl-N-toluyl)homocysteine]methyl ester, [(S-phenyl-N-toluyl)homocysteine]methyl ester, [(S-benzyl-N-toluyl)homocysteine]methyl ester, [(S-phenylethyl-N-toluyl)homocysteine]methyl ester, [(S-pyridyl-N-toluyl)homocysteine]methyl ester, [(S-quinolyl-N-toluyl)homocysteine]methyl ester, [(S-naphthyl-N-toluyl)homocysteine]methyl ester, [(N-toluyl-S-biphenyl)homocysteine]methyl ester, [(S-ethyl-N-methoxybenzoyl)homocysteine]methyl ester, [(N-methoxybenzoyl-S-propyl)homocysteine]methyl ester, [(S-butyl-N-methoxybenzoyl)homocysteine]methyl ester, [(N-methoxybenzoyl-S-phenyl)homocysteine]methyl ester, [(S-benzyl-N-methoxybenzoyl)homocysteine]methyl ester, [(N-methoxybenzoyl-S-phenylethyl)homocysteine]methyl ester, [(N-methoxybenzoyl-S-pyridyl)homocysteine]methyl ester, [(N-methoxybenzoyl-S-quinolyl)homocysteine]methyl ester, [(N-methoxybenzoyl-S-naphthyl)homocysteine]methyl ester, [(S-biphenyl-N-methoxybenzyl)homocysteine]methyl ester, [(N-biphenylcarbonyl-S-ethyl)homocysteine]methyl ester, [(N-biphenylcarbonyl-S-propyl)homocysteine]methyl ester, [(N-biphenylcarbonyl-S-butyl)homocysteine]methyl ester, [(N-biphenylcarbonyl-S-phenyl)homocysteine]methyl ester, [(N-biphenylcarbonyl-S-benzyl)homocysteine]methyl ester, [(N-biphenylcarbonyl-S-phenylethyl)homocysteine]methyl ester, [(N-biphenylcarbonyl-S-pyridyl)homocysteine]methyl ester, [(N-biphenylcarbonyl-S-quinolyl)homocysteine]methyl ester, [(N-biphenylcarbonyl-S-naphthyl)homocysteine]methyl ester, [(N-biphenylcarbonyl-S-biphenyl)homocysteine]methyl ester, [(N-benzylcarbonyl-S-ethyl)homocysteine]methyl ester, [(N-benzylcarbonyl-S-propyl)homocysteine]methyl ester, [(N-benzylcarbonyl-S-butyl)homocysteine]methyl ester, [(N-benzylcarbonyl-S-phenyl)homocysteine]methyl ester, [(N-benzylcarbonyl-S-benzyl)homocysteine]methyl ester, [(N-benzylcarbonyl-S-phenylethyl)homocysteine]methyl ester, [(N-benzylcarbonyl-S-pyridyl)homocysteine]methyl ester, [(N-benzylcarbonyl-S-quinolyl)homocysteine]methyl ester, [(N-benzylcarbonyl-S-naphthyl)homocysteine]methyl ester, [(N-benzylcarbonyl-S-biphenyl)homocysteine]methyl ester, stereoisomers of the compounds, or pharmacologically acceptable salts thereof.

Of the compounds represented by the general formula (2), specific examples of the compounds which are not included in the general formula (3) and (4) include (N-acetyl-N-benzoyl-S-methyl)cysteine, (N-benzoyl-N-propionyl-S-methyl)cysteine, (N-benzoyl-N-butyryl-S-methyl)cysteine, (N-acetyl-N-toluyl-S-methyl)cysteine, (S-methyl-N-propionyl-N-toluyl)cysteine, (N-butyryl-S-methyl-N-toluyl)cysteine, (N-acetyl-S-methyl-N-methoxybenzoyl)cysteine, (N-methoxybenzoyl-S-methyl-N-propionyl)cysteine, (N-butyryl-N-methoxybenzoyl-S-methyl)cysteine, (N-acetyl-N-biphenylcarbonyl-S-methyl)cysteine, (N-biphenylcarbonyl-S-methyl-N-propionyl)cysteine, (N-butyryl-N-biphenylcarbonyl-S-methyl)cysteine, (N-acetyl-N-benzylcarbonyl-S-methyl)cysteine, (N-propionyl-N-benzylcarbonyl-S-methyl)cysteine, (N-butyryl-N-benzylcarbonyl-S-methyl)cysteine, (N-acetyl-N-benzoyl)methionine, (N-benzoyl-N-propionyl)methionine, (N-benzoyl-N-butyryl)methionine, (N-acetyl-N-toluyl)methionine, (N-propionyl-N-toluyl)methionine, (N-butyryl-N-toluyl)methionine, (N-acetyl-N-methoxybenzoyl)methionine, (N-methoxybenzoyl-N-propionyl)methionine, (N-butyryl-N-methoxybenzoyl)methionine, (N-acetyl-N-biphenylcarbonyl)methionine, (N-biphenylcarbonyl-N-propionyl)methionine, (N-butyryl-N-biphenylcarbonyl)methionine, (N-acetyl-N-benzylcarbonyl)methionine, (N-propionyl-N-benzylcarbonyl)methionine, (N-butyryl-N-benzylcarbonyl)methionine, stereoisomers of the compounds, or pharmacologically acceptable salts thereof.

Out of the compounds represented by the general formula (1), the compounds represented by the general formula (5) and (6) are described. Any of the compounds represented by the general formula (5) and (6) is a novel compound.

[Chem. 14]

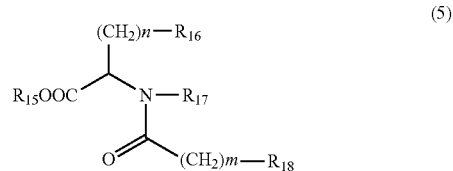

(5)

In the general formula (5), $R_{15}$ represents a hydrogen atom or a linear or branched alkyl group having 1 to 8 carbon atoms; $R_{16}$ represents —$SO_3H$ or —$SO_2$—$X_4$, provided that the $X_4$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{17}$ represents a hydrogen atom or an acyl group having a linear or branched alkyl chain having 1 to 8 carbon atoms; $R_{18}$ represents an optionally unsubstituted or substituted aromatic group or polycyclic condensed aromatic group having 5 to 12 carbon atoms; m represents an integer of 0 to 3; and n represents an integer of 1 or 2.

[Chem. 15]

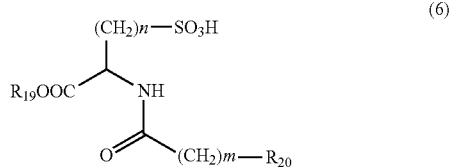

(6)

In the general formula (6), $R_{19}$ represents a hydrogen atom or a linear or branched alkyl group having 1 to 8 carbon atoms; $R_{20}$ represents an optionally unsubstituted or substituted aromatic group or polycyclic condensed aromatic group having 5 to 12 carbon atoms; m represents an integer of 0 to 3; and n represents an integer of 1 or 2.

As described above, the general formula (5) is a preferred form of the general formula (1) and the general formula (6) is a more preferred form of the general formula (1). Specific examples of the compound represented by the general formula (6) include N-(benzoyl)cysteic acid, N-(toluyl)cysteic acid, N-(ethylbenzoyl)cysteic acid, N-(propylbenzoyl)cysteic acid, N-(butylbenzoyl)cysteic acid, N-(pentylbenzoyl) cysteic acid, N-(hexylbenzoyl)cysteic acid, N-(heptylbenzoyl)cysteic acid, N-(octylbenzoyl)cysteic acid, N-(methoxybenzoyl)cysteic acid, N-(ethoxybenzoyl)cysteic acid, N-(propyloxybenzoyl)cysteic acid, N-(butyloxybenzoyl)cysteic acid, N-(hydroxybenzoyl)cysteic acid, N-(aminobenzoyl)cysteic acid, N—(N'-methylaminobenzoyl)cysteic acid, N—(N'-ethylaminobenzoyl)cysteic acid, N—(N',N'-dimethylaminobenzoyl)cysteic acid, N—(N',N'-diethylaminobenzoyl)cysteic acid, N-(fluorobenzoyl)cysteic acid, N-(trifluoromethylbenzoyl)cysteic acid, N-(chlorobenzoyl)cysteic acid, N-(dichlorobenzoyl)cysteic acid, N-(nitrobenzoyl)cysteic acid, (N-cyanobenzoyl)cysteic acid, N-carboxybenzoyl)cysteic acid, N-(methoxycarbonylbenzoyl)cysteic acid, N-(ethoxycarbonylobenzoyl)cysteic acid, N-(acetylbenzoyl)cysteic acid, N-(propionylbenzoyl)cysteic acid, N-(butyrylbenzoyl)cysteic acid, N-(naphthoyl)cysteic acid, N-(methylnaphthoyl)cysteic acid, N-(methoxynaphthoyl)cysteic acid, N-(hydroxynaphthoyl)cysteic acid, N-(aminonaphthoyl)cysteic acid, N-(acetylnaphthoyl)cysteic acid, N-(fluoronaphthoyl)cysteic acid, N-(methoxycarbonylnaphthoyl)cysteic acid, (N-biphenylcarbonyl)cysteic acid, (N-methoxybiphenylcarbonyl)cysteic acid, N-(benzylcarbonyl)cysteic acid, N-(phenylethylcarbonyl)cysteic acid, N-(phenylpropylcarbonyl)cysteic acid, N-(phenylbutylcarbonyl)cysteic acid, N-(toluylmethylcarbonyl)cysteic acid, N-(toluylethylcarbonyl)cysteic acid, N-(toluylpropylcarbonyl)cysteic acid, N-(toluylbutylcarbonyl)cysteic acid, N-(pyridinecarbonyl)cysteic acid, N-(quinolinecarbonyl)cysteic acid, (N-benzoylcysteic acid)methyl ester, (N-benzoylcysteic acid)ethyl ester, (N-benzoylcysteic acid)propyl ester, (N-benzoylcysteic acid)butyl ester, (N-toluyl cysteic acid) methyl ester, (N-toluyl cysteic acid)ethyl ester, (N-toluyl cysteic acid)propyl ester, (N-toluyl cysteic acid)butyl ester, [(N-toluyl)cysteic acid]methyl ester, [(N-toluyl)cysteic acid] ethyl ester, [(N-toluyl)cysteic acid]propyl ester, [(N-methoxybenzoyl)cysteic acid]methyl ester, [(N-methoxybenzoyl)cysteic acid]ethyl ester, [(N-methoxybenzoyl)cysteic acid]propyl ester, [(N-biphenylcarbonyl)cysteic acid]methyl ester, [(N-biphenylcarbonyl)cysteic acid]ethyl ester, [(N-biphenylcarbonyl)cysteic acid]propyl ester, [(N-benzylcarbonyl)cysteic acid]methyl ester, [(N-benzylcarbonyl)cysteic acid]ethyl ester, [(N-benzylcarbonyl) cysteic acid]propyl ester, N-(benzoyl)homocysteic acid, N-(toluyl)homocysteic acid, N-(ethylbenzoyl)homocysteic acid, N-(propylbenzoyl)homocysteic acid, N-(butylbenzoyl) homocysteic acid, N-(pentylbenzoyl)homocysteic acid, N-(hexylbenzoyl)homocysteic acid, N-(heptylbenzoyl)homocysteic acid, N-(octylbenzoyl)homocysteic acid, N-(methoxybenzoyl)homocysteic acid, N-(ethoxybenzoyl) homocysteic acid, N-(propyloxybenzoyl)homocysteic acid, N-(butyloxybenzoyl)homocysteic acid, N-(hydroxybenzoyl) homocysteic acid, N-(aminobenzoyl)homocysteic acid, N—(N'-methylaminobenzoyl)homocysteic acid, N—(N'-ethylaminobenzoyl)homocysteic acid, N—(N',N'-dimethylaminobenzoyl)homocysteic acid, N—(N',N'-diethylaminobenzoyl)homocysteic acid, N-(fluorobenzoyl) homocysteic acid, N-(trifluoromethylbenzoyl)homocysteic acid, N-(chlorobenzoyl)homocysteic acid, N-(dichlorobenzoyl)homocysteic acid, N-(nitrobenzoyl)homocysteic acid, (N-cyanobenzoyl)homocysteic acid, N-(carboxybenzoyl)homocysteic acid, N-(methoxycarbonylbenzoyl)homocysteic acid, N-(ethoxycarbonylbenzoyl)homocysteic acid, N-(acetylbenzoyl)homocysteic acid, N-(propionylbenzoyl) homocysteic acid, N-(butyrylbenzoyl)homocysteic acid, N-(naphthoyl)homocysteic acid, N-(methylnaphthoyl)homocysteic acid, N-(methoxynaphthoyl)homocysteic acid, N-(hydroxynaphthoyl)homocysteic acid, N-(aminonaphthoyl)homocysteic acid, N-(acetylnaphthoyl)homocysteic acid, N-(fluoronaphthoyl)homocysteic acid, N-(methoxycarbonylnaphthoyl)homocysteic acid, N-(biphenylcarbonyl)homocysteic acid, N-(methoxybiphenylcarbonyl)homocysteic acid, N-(benzylcarbonyl)homocysteic acid, N-(phenylethylcarbonyl)homocysteic acid, N-(phenylpropylcarbonyl)homocysteic acid, N-(phenylbutylcarbonyl)homocysteic acid, N-(phenylpentylcarbonyl)homocysteic acid, N-(naphthylmethylcarbonyl)homocysteic acid, N-(naphthylethylcarbonyl) homocysteic acid, N-(pyridinecarbonyl)homocysteic acid, N-(quinolinecarbonyl)homocysteic acid, [N-(benzoyl)homocysteic acid]methyl ester, [N-(benzoyl)homocysteic acid] ethyl ester, [N-(benzoyl)homocysteic acid]propyl ester, [N-(benzoyl)homocysteic acid]butyl ester, [N-(toluyl) homocysteic acid]methyl ester, [N-(toluyl)homocysteic acid] ethyl ester, [N-(toluyl)homocysteic acid]propyl ester, [N-(toluyl)homocysteic acid]butyl ester, [N-(methoxybenzoyl) homocysteic acid]methyl ester, [N-(methoxybenzoyl) homocysteic acid]ethyl ester, [N-(methoxybenzoyl) homocysteic acid]propyl ester, [N-(methoxybenzoyl) homocysteic acid]butyl ester, [N-(biphenylcarbonyl) homocysteic acid]methyl ester, [N-(biphenylcarbonyl) homocysteic acid]ethyl ester, [N-(biphenylcarbonyl) homocysteic acid]propyl ester, [N-(biphenylcarbonyl) homocysteic acid]butyl ester, [N-(benzylcarbonyl) homocysteic acid]methyl ester, [N-(benzylcarbonyl) homocysteic acid]ethyl ester, [N-(benzylcarbonyl) homocysteic acid]propyl ester, [N-(benzylcarbonyl) homocysteic acid]butyl ester, stereoisomers of the compounds described above, and/or pharmacologically acceptable salts thereof. Of those, more preferred are N-(benzoyl)cysteic acid, N-(toluyl)cysteic acid, N-(methoxybenzoyl)cysteic acid, N-(biphenylcarbonyl)cysteic acid, N-(benzylcarbonyl)cysteic acid, N-(benzoyl)homocysteic acid, N-(toluyl)homocysteic acid, N-(methoxybenzoyl)homocysteic acid, N-(biphenylcarbonyl)homocysteic acid, N-(benzylcarbonyl)homocysteic acid, stereoisomers of the compounds, pharmacologically acceptable salts thereof, and the like.

Of the compounds represented by the general formula (5), specific examples of the compounds which are not included in the general formula (6) include (N-acetyl-N-benzoyl)cysteic acid, (N-benzoyl-N-propionyl)cysteic acid, (N-benzoyl-N- butyryl)cysteic acid, (N-benzoyl-N-isobutyryl)cysteic acid, (N-benzoyl-N-valeryl)cysteic acid, (N-benzoyl-N-isovaleryl)cysteic acid, (N-benzoyl-N-pivaloyl)cysteic acid, (N-benzoyl-N-hexanoyl)cysteic acid, (N-benzoyl-N-octanoyl)cysteic acid, (N-acetyl-N-toluyl)cysteic acid, (N-propionyl-N-toluyl)cysteic acid, (N-butyryl-N-toluyl)cysteic acid, (N-isobutyryl-N-toluyl)cysteic acid, (N-toluyl-N-valeryl)cysteic acid, (N-isovaleryl-N-toluyl)cysteic acid, (N-pivaloyl-N-toluyl)cysteic acid, (N-hexanoyl-N-toluyl)cysteic acid, (N-octanoyl-N-toluyl)cysteic acid, (N-acetyl-N-methoxybenzoyl)cysteic acid, (N-methoxybenzoyl-N-propionyl)cysteic acid, (N-butyryl-N-methoxybenzoyl)cysteic acid, (N-isobutyryl-N-methoxybenzoyl)cysteic acid, (N-methoxybenzoyl-N-valeryl)cysteic acid, (N-isovaleryl-N-methoxybenzoyl)cysteic acid, (N-methoxybenzoyl-N-pivaloyl)cysteic acid, (N-hexanoyl-N-methoxybenzoyl)cysteic acid, (N-methoxybenzoyl-N-octanoyl)cysteic acid, (N-acetyl-N-biphenylcarbonyl)cysteic acid, (N-biphenylcarbonyl-N-propionyl)cysteic acid, (N-biphenylcarbonyl-N-butyryl)cysteic acid, (N-biphenylcarbonyl-N-isobutyryl)cysteic acid, (N-biphenylcarbonyl-N-valeryl)cysteic acid, (N-biphenylcarbonyl-N-isovaleryl)cysteic acid, (N-biphenylcarbonyl-N-pivaloyl)cysteic acid, (N-biphenylcarbonyl-N-hexanoyl)cysteic acid, (N-biphenylcarbonyl-N-octanoyl)cysteic acid, (N-acetyl-N-benzylcarbonyl)cysteic acid, (N-benzylcarbonyl-N-propionyl)cysteic acid, (N-benzylcarbonyl-N-butyryl)cysteic acid, (N-benzylcarbonyl-N-isobutyryl)cysteic acid, (N-benzylcarbonyl-N-valeryl)cysteic acid, (N-benzylcarbonyl-N-isovaleryl)cysteic acid, (N-benzylcarbonyl-N-pivaloyl)cysteic acid, (N-benzylcarbonyl-N-hexanoyl)cysteic acid, (N-benzylcarbonyl-N-octanoyl)cysteic acid, (N-acetyl-N-benzoyl)homocysteic acid, (N-benzoyl-N-propionyl)homocysteic acid, (N-benzoyl-N-butyryl)homocysteic acid, (N-benzoyl-N-valeryl)homocysteic acid, (N-benzoyl-N-pivaloyl)homocysteic acid, (N-benzoyl-N-hexanoyl)homocysteic acid, (N-benzoyl-N-octanoyl)homocysteic acid, (N-acetyl-N-toluyl)homocysteic acid, (N-propionyl-N-toluyl)homocysteic acid, (N-butyryl-N-toluyl)homocysteic acid, (N-acetyl-N-methoxybenzoyl)homocysteic acid, (N-propionyl-N-methoxybenzoyl)homocysteic acid, (N-butyryl-N-methoxybenzoyl)homocysteic acid, (N-acetyl-N-biphenylcarbonyl)homocysteic acid, (N-biphenylcarbonyl-N-propionyl)homocysteic acid, (N-biphenylcarbonyl-N-toluyl)homocysteic acid, (N-acetyl-N-benzylcarbonyl)homocysteic acid, (N-benzylcarbonyl-N-propionyl)homocysteic acid, (N-benzylcarbonyl-N-butyryl)homocysteic acid, stereoisomers of the compounds described above, or pharmacologically acceptable salts thereof.

The compounds represented by the general formula (1) to (6) have excellent wrinkle-reducing effects on wrinkles formed by ultraviolet rays exposure and the like, and the wrinkle-reducing effects are expressed through procollagen production-promoting actions. In addition, the wrinkle-reducing effects are also estimated to be expressed through inhibiting actions on matrix metalloproteases such as MMP1, MMP9, and MMP13 or inhibitory actions on the production of cytokines such as IL-1 and IL-6.

The compounds represented by the general formula (1) to (6) may be manufactured using commercially available reagents as raw materials in accordance with methods of production examples as described later. Such compounds may each be directly utilized as the wrinkle-reducing agent of the present invention. Alternatively, the compounds are converted into the form of salts by treatments with pharmacologically acceptable acids or bases, and the salts may be used. Suitable examples of the salts include: mineral acid salts such as a hydrochloride, a sulfate, a nitrate, a phosphate, and a carbonate; organic acid salts such as a maleate, a fumarate, an oxalate, a citrate, a lactate, a tartrate, a methanesulfonate, a para-toluenesulfonate, and a benzenesulfonate; alkali metal salts such as a sodium salt and a potassium salt; alkali earth metal salts such as a calcium salt and a magnesium salt; organic amine salts such as a triethylamine salt, a triethanolamine salt, an ammonium salt, a monoethanolamine salt, and a piperidine salt; and basic amino acid salts such as a lysine salt and an alginate.

Hereinafter, production examples of the wrinkle-reducing agent of the present invention are described.

Production Example 1

Synthesis of Compound 1

[Chem. 16]

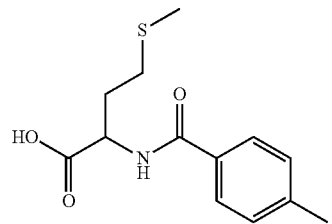

N-(toluyl)methionine (Compound 1)

In a recovery flask having a volume of 100 (mL) were placed by 5 (g) (33.5 mmol) of L-methionine (Wako Pure Chemical Industries, Ltd.), 20 (mL) of 1,4-dioxane (Wako Pure Chemical Industries, Ltd.), and 10 (mL) of water, and the flask was then cooled in an ice bath. After sufficient cooling, 9.21 (mL) of an 8 (N) sodium hydroxide aqueous solution and 4.21 (mL) of p-toluyl chloride (Sigma-Aldrich Co.) were successively dropped while the solution temperature being prevented from rising. After the completion of dropping, the ice bath was removed and the mixture was stirred at room temperature. The progress of the reaction was checked by thin layer chromatography, and 1,4-dioxane was then removed by evaporation under reduced pressure. The resultant residue was washed with ethyl acetate, and the pH was then adjusted to 2 or less with hydrochloric acid. The precipitated crystals were dissolved and extracted with ethyl acetate and then washed with a saturated sodium chloride aqueous solution and dried with anhydrous sodium sulfate. The resultant ethyl acetate solution was concentrated for crystallization. The resultant crystals were washed with diisopropyl ether and then filtered and dried to afford 6.99 (g) (26.1 mmol) of Compound 1 having the above-mentioned structure. Physicochemical properties are as described below.

$^1$H-NMR (CDCl$_3$): δ 2.13 (3H, s), 2.18 (1H, m), 2.35 (1H, m), 2.40 (3H, s), 2.66 (2H, t), 4.91 (1H, q), 7.13 (1H, d), 7.24 (2H, d), 7.71 (2H, d).

FAB-MS (positive ion mode): M/z=268 ([M+H]$^+$)

Production Example 2

Synthesis of Compound 2

[Chem. 17]

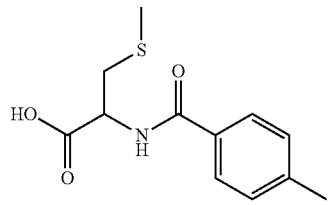

[S-methyl-N-toluyl]cysteine (Compound 2)

In a recovery flask having a volume of 100 (mL) were placed by 5 (g) (37.0 mmol) of S-methyl-L-cysteine (Tokyo Chemical Industry Co., Ltd.), 20 (mL) of 1,4-dioxane (Wako Pure Chemical Industries, Ltd.), and 10 (mL) of water, and the flask was then cooled in an ice bath. After sufficient cooling, 10.2 (mL) of an 8 (N) sodium hydroxide aqueous solution and 4.9 (mL) of p-toluyl chloride (Sigma-Aldrich Co.) were successively dropped while the solution temperature being prevented from rising. After the completion of dropping, the ice bath was removed and the mixture was stirred at room temperature. The progress of the reaction was checked by thin layer chromatography, and 1,4-dioxane was then removed by evaporation under reduced pressure. The resultant residue was washed with ethyl acetate, and the pH was then adjusted to 2 or less with hydrochloric acid. The precipitated crystals were dissolved and extracted with ethyl acetate and then washed with a saturated sodium chloride aqueous solution and dried with anhydrous sodium sulfate. The resultant ethyl acetate solution was concentrated for crystallization. The resultant crystals were washed with diisopropyl ether and then filtered and dried to afford crude crystals. The resultant crude crystals were suspended in ethyl acetate, and the temperature was increased to 60° C. After complete dissolution had been confirmed, 40 (mL) of diisopropyl ether were dropped to precipitate crystals. The suspension was left to be cooled to room temperature and then filtered and dried to afford 2.87 (g) (11.3 mmol) of Compound 2 having the above-mentioned structure. Physicochemical properties are as described below.

$^1$H-NMR (CDCl$_3$): δ 2.16 (3H, s), 2.40 (3H, s), 3.15 (2H, m), 4.98 (1H, q), 7.09 (1H, d), 7.25 (2H, d), 7.72 (2H, d).

FAB-MS (positive ion mode): M/z=254 ([M+H]$^+$), 276 ([M+Na]$^+$)

Production Example 3

Synthesis of Compound 3

[Chem. 18]

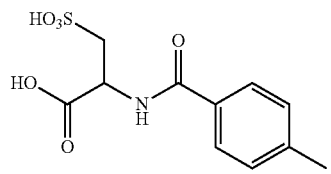

N-(toluyl)cysteic acid (Compound 3)

In a recovery flask having a volume of 100 (mL) were placed by 5 (g) (26.7 mmol) of L-cysteic acid monohydrate (Sigma-Aldrich Co.), 20 (mL) of 1,4-dioxane (Wako Pure Chemical Industries, Ltd.), and 10 (mL) of water, and the flask was then cooled in an ice bath. After sufficient cooling, 10.7 (mL) of an 8 (N) sodium hydroxide aqueous solution and 3.36 (mL) of p-toluyl chloride (Sigma-Aldrich Co.) were successively dropped while the solution temperature being prevented from rising. After the completion of dropping, the ice bath was removed and the mixture was stirred at room temperature. The progress of the reaction was checked by thin layer chromatography, and 1,4-dioxane was then removed by evaporation under reduced pressure. The resultant residue was washed with ethyl acetate, and the pH was then adjusted to 2 or less with hydrochloric acid. The resultant aqueous solution was lyophilized and a target material was extracted with methanol. After methanol had been removed by evaporation under reduced pressure, crystallization and filtration were performed. The crystals collected by filtration were dried to afford 5.79 (g) (20.2 mmol) of Compound 3 having the above-mentioned structure. Physicochemical properties are as described below.

$^1$H-NMR (D$_2$O): δ 2.32 (3H, s), 3.46 (2H, m), 4.87 (1H, m), 7.25 (2H, d), 7.64 (2H, d).

FAB-MS (negative ion mode): M/z=286 ([M−H]$^-$), 308 ([M+Na—H]$^-$)

Production Example 4

Synthesis of Compound 4

[Chem. 19]

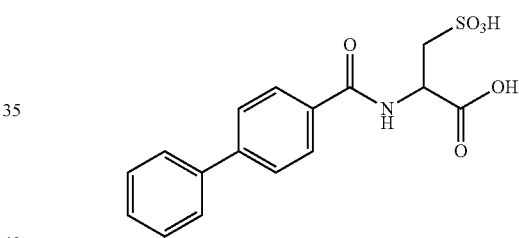

N-(4-phenylbenzoyl)-L-cysteic acid (Compound 4)

In a recovery flask having a volume of 100 (mL) were placed by 2 (g) (11.8 mmol) of L-cysteic acid (Tokyo Chemical Industry Co., Ltd.), 12 (mL) of tetrahydrofuran (Wako Pure Chemical Industries, Ltd.), and 12 (mL) of water, and the flask was then cooled in an ice bath. After sufficient cooling, 2.94 (g) (21.3 mmol) of potassium carbonate (Wako Pure Chemical Industries, Ltd.) and 2.05 (g) of 4-phenylbenzoyl chloride (Tokyo Chemical Industry Co., Ltd.) were successively added while the solution temperature being prevented from rising. A reaction was performed under the ice bath for 1.5 hours, and 1.02 (g) of 4-phenylbenzoyl chloride (Tokyo Chemical Industry Co., Ltd.) were then added again. After the addition, the ice bath was removed and the mixture was stirred at room temperature. The progress of the reaction was checked by thin layer chromatography, and tetrahydrofuran was then removed by evaporation under reduced pressure. The resultant residue was washed with ethyl acetate, and the pH was adjusted to 2 or less with hydrochloric acid. The precipitated crystals were filtered and washed with water. The resultant crystals were washed by suspending them in acetone and then filtered. The crystals collected by filtration were dried at 60° C. to afford 2.37 (g) (6.78 mmol) of Compound 4 having the above-mentioned structure. Physicochemical properties are as described below.

$^1$H-NMR (DMSO-d6): δ 2.96 (2H, m), 4.54 (1H, q), 7.42 (1H, m), 7.51 (2H, m), 7.74 (2H, d), 7.80 (2H, d), 7.90 (2H, d), 8.94 (1H, d).

FAB-MS (negative ion mode): M/z=348 ([M−H]−)

Production Example 5

Synthesis of Compound 5

[Chem. 20]

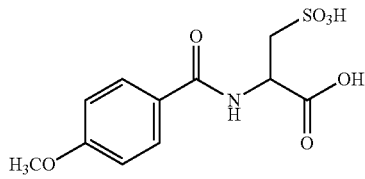

N-(4-methoxybenzoyl)-L-cysteic acid (Compound 5)

In a recovery flask having a volume of 100 (mL) were placed by 2 (g) (11.8 mmol) of L-cysteic acid (Tokyo Chemical Industry Co., Ltd.), 12 (mL) of tetrahydrofuran (Wako Pure Chemical Industries, Ltd.), and 12 (mL) of water, and the flask was then cooled in an icebath. After sufficient cooling, 2.94 (g) (21.3 mmol) of potassium carbonate (Wako Pure Chemical Industries, Ltd.) and 1.61 (g) of 4-methoxybenzoyl chloride (Tokyo Chemical Industry Co., Ltd.) were successively added while the solution temperature being prevented from rising. A reaction was performed under the ice bath for 1 hour, and 0.81 (g) of 4-methoxybenzoyl chloride (Tokyo Chemical Industry Co., Ltd.) were then added again. After the addition, the ice bath was removed and the mixture was stirred at room temperature. The progress of the reaction was checked by thin layer chromatography, and tetrahydrofuran was then removed by evaporation under reduced pressure. The resultant residue was washed with ethyl acetate, and the pH was adjusted to 2 or less with hydrochloric acid. The precipitated crystals were filtered and washed with water. The filtrate was concentrated and the precipitated crystals were filtered again. The resultant crystals were combined and then washed by suspending them in acetone. The crystals were filtered and the crystals collected by filtration were then dried at 60° C. to afford 2.47 (g) (8.14 mmol) of Compound 5 having the above-mentioned structure. Physicochemical properties are as described below.

$^1$H-NMR (D$_2$O): δ 3.45 (2H, m), 3.81 (3H, s), 4.85 (1H, m), 7.00 (2H, d), 7.72 (2H, d).

FAB-MS (negative ion mode): M/z=302 ([M−H]−)

Production Example 6

Synthesis of Compound 6

[Chem. 21]

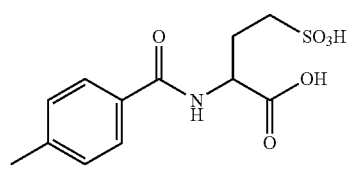

N-toluyl-DL-homocysteic acid (Compound 6)

In a recovery flask having a volume of 100 (mL) were placed by 2 (g) (10.9 mmol) of DL-homocysteic acid (Sigma-Aldrich Co.), 12 (mL) of tetrahydrofuran (Wako Pure Chemical Industries, Ltd.), and 12 (mL) of water, and the flask was then cooled in an ice bath. After sufficient cooling, 2.71 (g) (19.6 mmol) of potassium carbonate (Wako Pure Chemical Industries, Ltd.) were added. 1.49 (g) of p-toluyl chloride (Sigma-Aldrich Co.) were successively added while the solution temperature being prevented from rising. A reaction was performed under the ice bath for 1 hour, and 0.76 (g) of p-toluyl chloride (Sigma-Aldrich Co.) were then added again. After the addition, the ice bath was removed and the mixture was stirred at room temperature. The progress of the reaction was checked by thin layer chromatography, and tetrahydrofuran was then removed by evaporation under reduced pressure. The resultant residue was washed with ethyl acetate, and the pH was adjusted to 2 or less with hydrochloric acid. The solution was filtered and the filtrate was then concentrated and supplemented with methanol. The precipitated crystals were separated by filtration and then washed by suspending them in water. The crystals were filtered and the crystals collected by filtration were dried at 60° C. to afford 1.95 (g) (6.47 mmol) of Compound 6 having the above-mentioned structure. Physicochemical properties are as described below.

$^1$H-NMR (DMSO-d6): δ 2.12 (2H, m), 2.35 (3H, s), 2.57 (2H, t), 4.37 (1H, m), 7.26 (2H, d), 7.79 (2H, d), 9.02 (1H, d).

FAB-MS (negative ion mode): M/z=300 ([M−H]−)

Production Example 7

Synthesis of Compound 7

[Chem. 22]

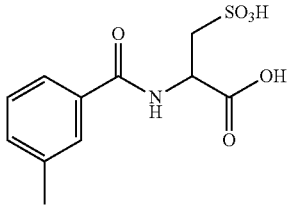

N-(m-toluyl)cysteic acid (Compound 7)

In a recovery flask having a volume of 100 (mL) were placed by 3 (g) (17.7 mmol) of L-cysteic acid (Tokyo Chemical Industry Co., Ltd.), 18 (mL) of tetrahydrofuran (Wako Pure Chemical Industries, Ltd.), and 18 (mL) of water, and the flask was then cooled in an ice bath. After sufficient cooling, 4.40 (g) (31.6 mmol) of potassium carbonate (Wako Pure Chemical Industries, Ltd.) and 2.19 (g) of m-toluyl, chloride (Tokyo Chemical Industry Co., Ltd.) were successively added while the solution temperature being prevented from rising. A reaction was performed under the ice bath for 1 hour, and 1.09 (g) of m-toluyl chloride (Tokyo Chemical Industry Co., Ltd.) were then added again. After the addition, the ice bath was removed and the mixture was stirred at room temperature. The progress of the reaction was checked by thin layer chromatography, and tetrahydrofuran was then removed by evaporation under reduced pressure. The resultant residue was washed with ethyl acetate, and the pH was adjusted to 2 or less with hydrochloric acid. The filtrate was concentrated and supplemented with water (18 ml). The precipitated crystals were separated by filtration. The resultant crystals were washed by suspending them in acetone and collected by filtration. The crystals collected by filtration were dried at 60°

C. to afford 1.65 (g) (5.74 mmol) of Compound 7 having the above-mentioned structure. Physicochemical properties are as described below.

$^1$H-NMR (DMSO-d6): δ 2.36 (3H, s), 2.94 (2H, m), 4.41 (1H, m), 7.36 (2H, d), 7.58 (2H, t), 8.84 (1H, d), 12.5 (1H, bs).

FAB-MS (negative ion mode): M/z=286 ([M−H]$^-$)

Production Example 8

Synthesis of Compound 8

[Chem. 23]

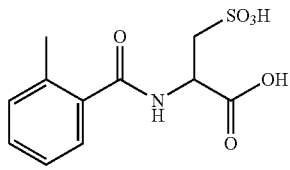

N-(o-toluyl)-L-cysteic acid (Compound 8)

In a recovery flask having a volume of 100 (mL) were placed by 3 (g) (17.7 mmol) of L-cysteic acid (Tokyo Chemical Industry Co., Ltd.), 18 (mL) of tetrahydrofuran (Wako Pure Chemical Industries, Ltd.), and 18 (mL) of water, and the flask was then cooled in an icebath. After sufficient cooling, 4.40 (g) (31.6 mmol) of potassium carbonate (Wako Pure Chemical Industries, Ltd.) were added. 3.28 (g) of o-toluyl chloride (Tokyo Chemical Industry Co., Ltd.) were successively added while the solution temperature being prevented from rising. After the addition, the ice bath was removed and the mixture was stirred at room temperature. The progress of the reaction was checked by thin layer chromatography, and tetrahydrofuran was then removed by evaporation under reduced pressure. The resultant residue was washed with ethyl acetate, and the pH was adjusted to 2 or less with hydrochloric acid. The filtrate was concentrated and supplemented with water (20 ml). The precipitated crystals were collected by filtration and the crystals were washed by suspending them in acetone. The crystals collected by filtration were dried at 60° C. to afford 0.78 (g) (2.72 mmol) of Compound 8 having the above-mentioned structure. Physicochemical properties are as described below.

$^1$H-NMR (D$_2$O): δ 2.31 (3H, s), 3.42 (2H, m), 4.86 (1H, m), 7.24 (2H, m), 7.35 (2H, m).

FAB-MS (negative ion mode): M/z=286 ([M−H]$^-$)

The above-mentioned production examples are merely illustrative of the methods for the manufacture of the compound represented by the general formula (1), and raw materials and reaction conditions may be appropriately modified to synthesize compounds excluding Compounds 1 to 8 above. The wrinkle-reducing agent of the present invention exhibits an excellent wrinkle-reducing action on wrinkles formed by ultraviolet rays exposure and the like, and hence is useful as an external preparation for skin. In order that the external preparation for skin exerts such action, the wrinkle-reducing agent according to the invention of the present application, i.e., each of the compounds represented by the general formula (1) to (6) is preferably incorporated in a total amount of 0.001% by mass to 20% by mass, more preferably 0.01% by mass to 10% by mass, still more preferably 0.1% by mass to 5% by mass with respect to the total amount of the external preparation for skin. When the content is less than 0.001% by mass with respect to the total amount of the external preparation for skin, an effect based on a wrinkle-reducing action may lower, whereas when the content exceeds 20% by mass, the effect may reach plateau, resulting in the needless impairment of a degree of freedom for prescription.

Some of the compounds represented by general formula (1) exert actions excluding an excellent wrinkle-reducing action on wrinkles formed by ultraviolet rays exposure and the like. Also in the case where the wrinkle-reducing agent of the present invention is incorporated into the external preparation for skin in order to express such actions, when a wrinkle-reducing effect is exhibited, the effect of the present invention is utilized. Thus, the external preparation for skin also falls within the technical range of the present invention. Examples of the actions excluding the wrinkle-reducing action include a moisture-retaining action, an actinic keratosis- or non-actinic keratosis-ameliorating action, a skin desquamation- or epidermal renewal-stimulating action, and an anti-aging action.

The external preparation for skin of the present invention can contain arbitrary ingredients used commonly in an external preparation for skin as well as the wrinkle-reducing agent of the present invention. Examples of such optional ingredients include: oils/waxes such as macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, glyceryl di-2-heptylundecanoate, glyceryl tri-2-ethylhexanoate, trimethylolpropane tri-2-ethylhexanoate, trimethylolpropane triisostearate, and pentane erythrite tetra-2-ethylhexanoate; chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexanesiloxane; modified polysiloxanes such as amino-modified polysiloxane, polyether-modified polysiloxane, alkyl-modified polysiloxane, and fluorine-modified polysiloxane; oil agents such as silicone oil; anionic surfactants such as fatty acid soaps (such as sodium laurate and sodium palmitate), potassium laurylsulfate, and triethanolamine alkylsulfate ether; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium hydroxide-1-carboxyethyloxy disodium salt), betaine-based surfactants (such as alkyl betaine, amide betaine, and sulfo betaine), and acylmethyl taurine; nonionic surfactants such as sorbitan fatty acid esters (such as sorbitan monostearate and sorbitan sesquioleate), glycerin fatty acid esters (such as glycerin monostearate), propyleneglycol fatty acid esters (such as propyleneglycol monostearate), cured castor oil derivatives, glycerol alkyl ether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glycerin monoisostearate), POE fatty acid esters (such as polyethyleneglycol monooleate and POE distearate), POE alkyl ethers (such as POE2-octyldodecyl ether), POE alkylphenyl ethers (such as POE nonylphenyl ether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glucoside; polyvalent alcohols such as polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexanediol, 1,2-hexanediol, and 1,2-octanediol; moisture-retaining ingredients such as sodium pyrrolidone carboxylate, lactate, and sodium lactate; fine particles such as mica, talc, kaolin, synthetic mica, calcium carbonate, magnesium carbonate, silicic anhydride (silica), aluminum oxide, and barium sulfate, whose surfaces may be treated; inorganic pigments such as red iron oxide, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic fine particles such as polyethylene powder, polymethyl methacrylate, nylon powder, and organopolysiloxane elastomer; p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl)benzotriazole and 4-methoxy-4'-t-butyldibenzoylmethane; lower alcohols such as ethanol and isopropanol; vitamins such as vitamin A or derivatives thereof; vitamin B types such as vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof; vitamin E types such as α-tocopherol, β-tocopherol, γ-tocopherol, and vitamin E acetate, vitamin D types, vitamin H, pantothenic acid, pantethine, and pyrroloquinoline quinone; and antibacterial agents such as phenoxyethanol.

The wrinkle-reducing agent of the present invention and the above-mentioned arbitrary ingredients may be treated in accordance with a conventional method to manufacture an external preparation for skin of the present invention such as a lotion, a milky liquid, an essence, a cream, a pack cosmetic, or a cleansing cosmetic. The external preparation for skin of the present invention may be applied without any particular limitation as long as being externally applied to the skin, and may be applied to cosmetics including quasi drugs, external medicines for skin, external goods for skin, and the like. In particular, cosmetics including quasi drugs are preferred. This is because the wrinkle-reducing agent of the present invention has high safety, which allows a continuous use.

Hereinafter, the present invention is described in more detail byway of examples, but it is needless to say that the present invention is not limited to those examples.

Example 1

Formulation Example 1

Wrinkle-Reducing Agent According to Compound 1

Compound 1 was synthesized by the above-mentioned method. Cosmetic 1 (lotion) containing the wrinkle-reducing agent of the present invention was prepared in accordance with the following prescription.

TABLE 1

| Ingredients | % by mass |
|---|---|
| Compound 1 | 0.5 |
| Ethanol (EtOH) | 99.5 |
| Total | 100 |

<Evaluation of Wrinkle-Reducing Effect of Compound 1 Using Photoaging Model>

A wrinkle-reducing effect of Cosmetic 1 above was evaluated in a test using a photoaging model.

A total of ten hairless mice, which were six-week-old at the time of the start of a test, were used and divided into two groups each consisting of five mice, i.e., a control group (ethanol solvent administration group) and a sample administration group. The dorsal portions of the hairless mice were irradiated with UVB at a frequency of once a day and three times a week for 10 consecutive weeks to induce photoaging. The UVB irradiation amount was set to 50 $mJ/cm^2$ for the first week and to 100 $mJ/cm^2$ on week 2 or later.

In the sample administration group, Cosmetic 1 above was administered to the dorsal portions of the hairless mice. Cosmetic 1 started to be administered to the dorsal portions of the hairless mice on the following day after the completion of the UVB irradiation for 10 weeks, and administered at a dose of 100 μL once a day for 8 weeks. In the control group, the same treatments were performed as those in sample administration group except that ethanol was administered in place of Cosmetic 1 (Lotion 1) in Table 1. Replicas were collected on Day 1 after the completion of the administration, and a scoring operation was performed by measurers in accordance with wrinkle score criteria (Table 2) using a replica image being projected under 30° oblique lighting and having a size of 2 cm by 2 cm in order to evaluate a wrinkle-reducing effect. The scoring operation was performed by three measurers separately and evaluated visually with scores of 1 to 6 at intervals of 0.5. An average value of the results was calculated.

TABLE 2

| Scores | Criteria for scores |
|---|---|
| 1 | No wrinkles are observed. |
| 2 | Shallow and short wrinkles are partially observed. |
| 3 | Shallow and long wrinkles are partially observed. |
| 4 | Shallow wrinkles are entirely observed. |
| 5 | Deep and long wrinkles are partially observed. |
| 6 | Deep and long wrinkles are entirely observed. |

FIG. 1 illustrates the wrinkle-reducing effect of Compound 1. The figure reveals that Compound 1 of the present invention has an excellent wrinkle-reducing effect.

Example 2

Formulation Examples 2 and 3

Wrinkle-Reducing Agents According to Compound 2 and Compound 3

Figure 2:
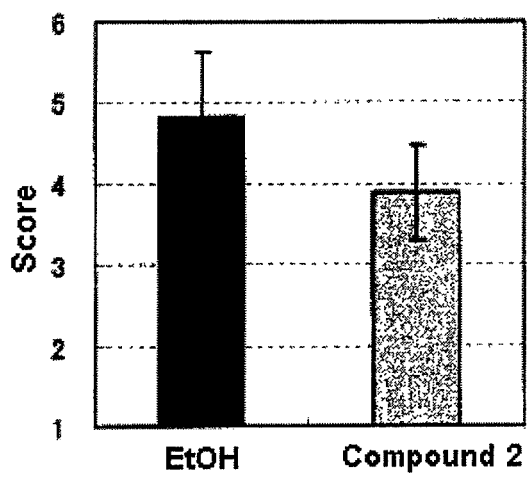
FIG. 2 is a graph illustrating a wrinkle-reducing action of Compound 2 in the present invention using a photoaging model.
Figure 3:
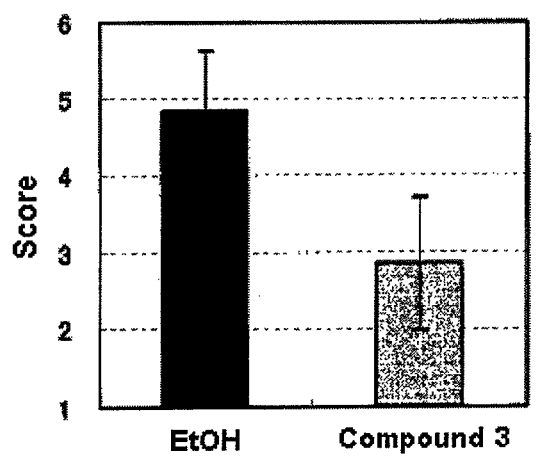
FIG. 3 is a graph illustrating a wrinkle-reducing action of Compound 3 in the present invention using a photoaging model.
Figure 4:
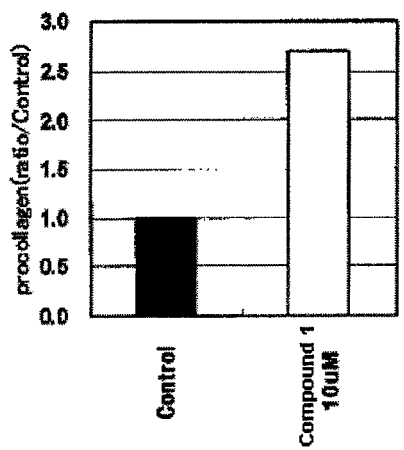
FIG. 4 are graphs illustrating procollagen-producing actions of Compounds 1 and 2 of the present invention.
Figure 4:
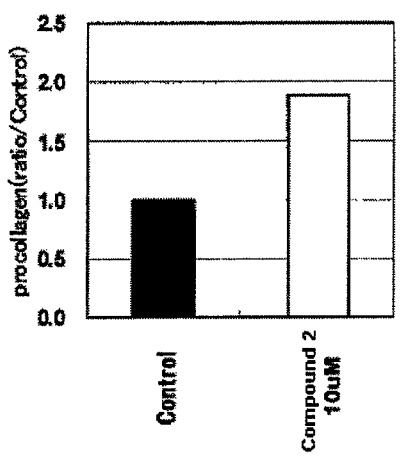
Figure 5:
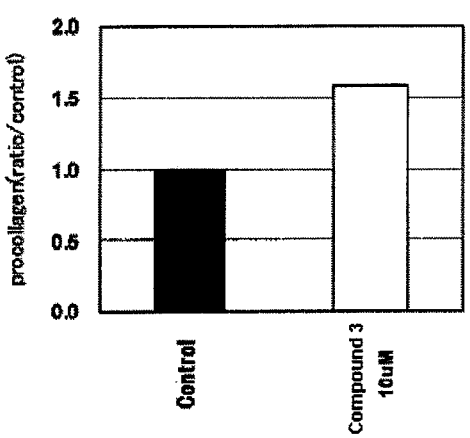
FIG. 5 are graphs illustrating procollagen-producing actions of Compounds 3 and 4 of the present invention.
Figure 5:
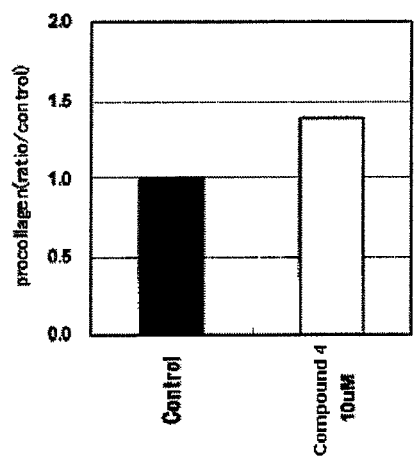
Figure 6:
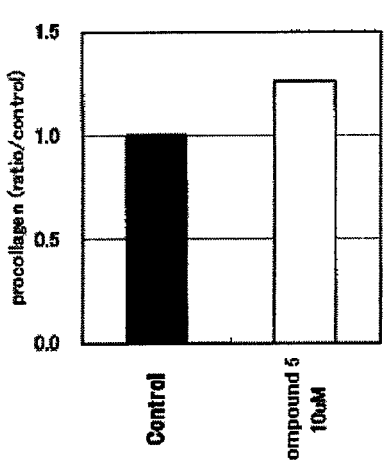
FIG. 6 are graphs illustrating procollagen-producing actions of Compounds 5 and 6 of the present invention.
Figure 6:
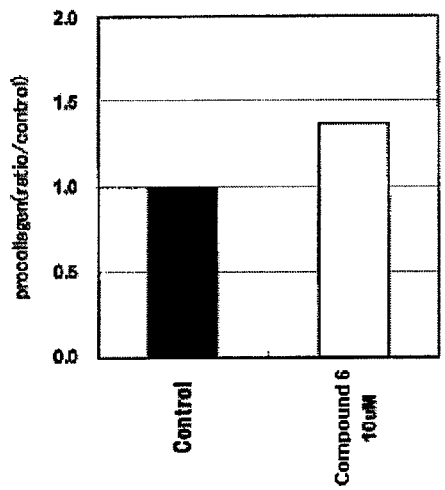
Figure 7:
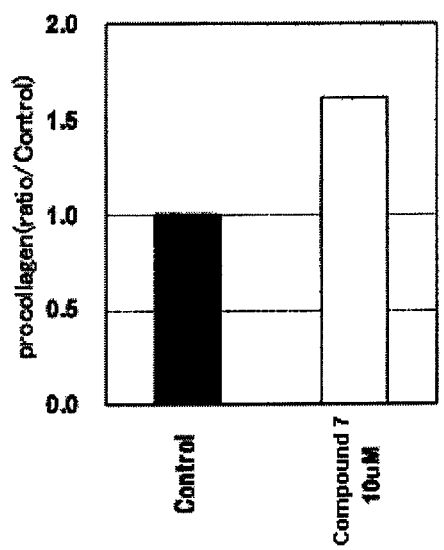
FIG. 7 are graphs illustrating procollagen-producing actions of Compounds 7 and 8 of the present invention.
Figure 7:
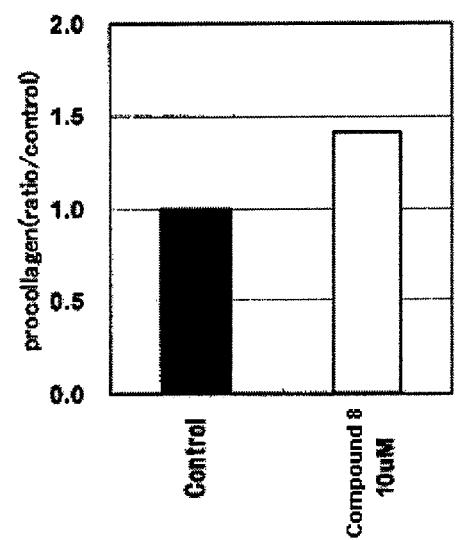

Compounds 2 and 3 were synthesized by the above-mentioned method. Cosmetic 2 and Cosmetic 3 were prepared by the same method as that in Example 1 except that Compounds 2 and 3 were used in place of Compound 1. In the same manner as in the case of Cosmetic 1, FIG. 2 and FIG. 3 illustrate the evaluation results of wrinkle-reducing actions. Those figures reveal that Compound 2 and Compound 3 of the present invention have excellent wrinkle-reducing effects.

Example 3

<Evaluation of Procollagen Production-Promoting Actions of Compounds 1 to 8>

Compounds 1 to 8 of the present invention were synthesized by the above-mentioned method to evaluate their procollagen production-promoting actions.

A keratinocyte growth medium (Humedia-KG 2 manufactured by KURABO INDUSTRIES LTD.) was used, and human-derived normal keratinocyte culture cells were seeded in a 24-well plate at $4.5 \times 10^4$ cells and cultured at 37° C. in 5% $CO_2$ for 4 days. Simultaneously, a DMEM medium (manufactured by SIGMA) supplemented with 10% FBS was used, and human-derived normal skin fibroblast culture cells were seeded in a 24-well plate at $2.5 \times 10^4$ cells and cultured at 37° C. in 5% $CO_2$.

Next, a medium, in which each of Compounds 1 to 8 was added at a final concentration of 10 μM to a DMEM medium (manufactured by SIGMA) supplemented with 2% FBS, was produced. Further, a medium, in which dimethylsulfoxide (manufactured by Sigma-Aldrich Co.) and 50% ethanol (manufactured by Sigma-Aldrich Co.) were added at final concentrations of $0.01 \times 10^{-3}$ (v/v %) in place of each of Compounds 1 to 8, was produced as a control.

After the cultured keratinocytes had been washed with PBS (manufactured by Wako Pure Chemical Industries, Ltd.), the medium was replaced with a medium containing each of the compounds and a medium containing dimethylsulfoxide and 50% ethanol, and culture was performed at 37° C. in 5% $CO_2$ for 24 hours. After 24 hours, the culture supernatant was collected.

After the cultured fibroblasts had been washed with PBS, the medium was replaced with the collected culture supernatant, and culture was performed at 37° C. in 5% $CO_2$ for 48 hours. After 48 hours, the fibroblasts had been washed with PBS, the medium was then replaced with a DMEM (manufactured by SIGMA), and culture was performed at 37° C. in 5% $CO_2$ for 2 hours. Then, the culture supernatant was collected. The amount of procollagen in the culture supernatant was measured by an ELISA method.

The fibroblasts cultured in the medium supplemented with dimethylsulfoxide and 50% ethanol were used as a control. FIGS. 4 to 7 illustrate ratios of procollagen production amounts of Compounds 1 to 8 with respect to the control.

The results of FIGS. 4 to 7 reveal that the compounds of the present invention have excellent procollagen production-promoting effects.

INDUSTRIAL APPLICABILITY

The wrinkle-reducing agent of the present invention is applicable to external preparations for skin such as cosmetics. The wrinkle-reducing agent has high safety, has an excellent wrinkle-reducing action, and hence is very useful as a raw material for cosmetics.

What is claimed is:

1. A wrinkle-reducing agent, comprising a compound represented by the following general formula (1), a stereoisomer of the compound or a pharmacologically acceptable salt thereof:

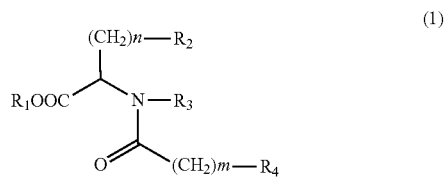

where: $R_1$ represents a hydrogen atom or a linear or branched alkyl group having 1 to 8 carbon atoms; $R_2$ represents —$SO_3H$, —$SO_2$—$X_4$, —$SO_2$—$NY_1$—$X_5$, or —$SO_2$—$NY_2$—$Y_3$, provided that the $X_1$ to $X_5$ each independently represent an aliphatic hydrocarbon group having 1 to 8 carbon atoms or an aromatic moiety having 5 to 12 carbon atoms, in which a heteroatom may be substituted for a hydrogen atom or a carbon atom, and the $Y_1$ to $Y_3$ each independently represent a hydrogen atom or a linear or branched alkyl group having 1 to 8 carbon atoms; $R_3$ represents a hydrogen atom or an acyl group having a linear or branched alkyl chain having 1 to 8 carbon atoms; $R_4$ represents a phenyl group, a toluoyl group, an ethylphenyl group, a propylphenyl group, a butylphenyl group, a pentylphenyl group, a hexylphenyl group, a methoxyphenyl group, an ethoxyphenyl group, a propyloxyphenyl group, a butyloxyphenyl group, a pentyloxyphenyl group, a hexyloxyphenyl group, a naphthyl group, a methylnaphthyl group, a methoxynaphthyl group, a biphenyl group, a pyridyl group, or a quinolyl group; m represents an integer of 0 to 3; and n represents an integer of 1 or 2.

2. The wrinkle-reducing agent according to claim 1, wherein $R_2$ represents —$SO_3H$ or —$SO_2$—$X_4$.

3. The wrinkle-reducing agent according to claim 1, wherein $R_2$ represents —$SO_3H$ and the $R_3$ represents a hydrogen atom.

4. A compound, which is represented by the following general formula (5), a stereoisomer of the compound, or a pharmacologically acceptable salt thereof:

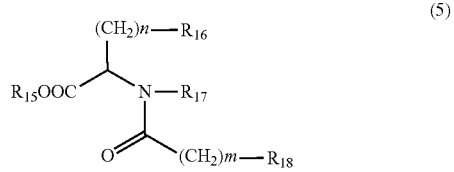

where: $R_{15}$ represents a hydrogen atom or a linear or branched alkyl group having 1 to 8 carbon atoms; $R_{16}$ represents —$SO_3H$ or —$SO_2$—$X_4$, provided that the $X_4$ represents an aliphatic hydrocarbon group having 1 to 8 carbon atoms or an aromatic moiety having 5 to 12 carbon atoms, in which a heteroatom may be substituted for a hydrogen atom or a carbon atom; $R_{17}$ represents a hydrogen atom or an acyl group having a linear or branched alkyl chain having 1 to 8 carbon atoms; $R_{18}$ represents a phenyl group, a toluoyl group, an ethylphenyl group, a propylphenyl group, a butylphenyl group, a pentylphenyl group, a hexylphenyl group, a methoxyphenyl group, an ethoxyphenyl group, a propyloxyphenyl group, a butyloxyphenyl group, a pentyloxyphenyl group, a hexyloxyphenyl group, a naphthyl group, a methylnaphthyl group, a methoxynaphthyl group, a biphenyl group, a pyridyl group, or a quinolyl group; m represents an integer of 0 to 3; and n represents an integer 1 or 2.

5. A compound, which is represented by the following general formula (6), a stereoisomer of the compound, or a pharmacologically acceptable salt thereof:

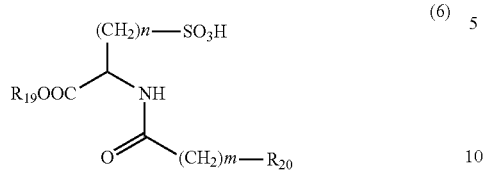

(6)

where: $R_{19}$ represents a hydrogen atom or a linear or branched alkyl group having 1 to 8 carbon atoms; $R_{20}$ represents a phenyl group, a toluoyl group, an ethylphenyl group, a propylphenyl group, a butylphenyl group, a pentylphenyl group, a hexylphenyl group, a methoxyphenyl group, an ethoxyphenyl group, a propyloxyphenyl group, a butyloxyphenyl group, a pentyloxyphenyl group, a hexyloxyphenyl group, a naphthyl group, a methylnaphthyl group, a methoxynaphthyl group, a biphenyl group, a pyridyl group, or a quinolyl group; m represents an integer of 0 to 3; and n represents an integer of 1 or 2.

6. An external preparation for skin, comprising the wrinkle-reducing agent according to any one of claims 1, 2 and 3 in an amount of 0.001 to 20% by mass.

7. A method for reducing a wrinkle, comprising administering a compound represented by the following general formula (1), a stereoisomer of the compound or a pharmacologically acceptable salt thereof to skin in need:

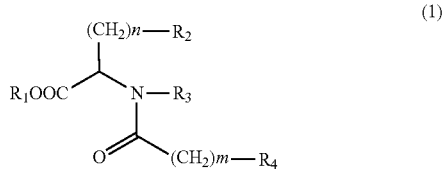

(1)

where: $R_1$ represents a hydrogen atom or a linear or branched alkyl group having 1 to 8 carbon atoms; $R_2$ represents —SH, —$SO_2$—$X_4$, —$SO_2$—$NY_1$—$X_5$, or —$SO_2$—$NY_2$—$Y_3$, provided that the $X_1$ to $X_5$ each independently represent an aliphatic hydrocarbon group having 1 to 8 carbon atoms or an aromatic moiety having 5 to 12 carbon atoms, in which a heteroatom may be substituted for a hydrogen atom or a carbon atom, and the $Y_1$ to $Y_3$ each independently represent a hydrogen atom or a linear or branched alkyl group having 1 to 8 carbon atoms; $R_3$ represents a hydrogen atom or an acyl group having a linear or branched alkyl chain having 1 to 8 carbon atoms; $R_4$ represents a phenyl group, a toluoyl group, an ethylphenyl group, a propylphenyl group, a butylphenyl group, a pentylphenyl group, a hexylphenyl group, a methoxyphenyl group, an ethoxyphenyl group, a propyloxyphenyl group, a butyloxyphenyl group, a pentyloxyphenyl group, a hexyloxyphenyl group, a naphthyl group, a methylnaphthyl group, a methoxynaphthyl group, a biphenyl group, a pyridyl group, or a quinolyl group; m represents an integer of 0 to 3; and n represents an integer of 1 or 2.

8. The method for reducing a wrinkle according to claim 7, wherein $R_2$ represents —S—$X_2$.

9. The method for reducing a wrinkle according to claim 7, wherein $R_2$ represents —S—$X_2$ and the $R_3$ represents a hydrogen atom.

10. The method for reducing a wrinkle according to claim 7, wherein $R_2$ represents —S—$X_2$, the $R_3$ represents a hydrogen atom, and the n represents 1.

11. The method for reducing a wrinkle according to claim 7, wherein $R_2$ represents —$SO_3H$ or —$SO_2$—$X_4$.

12. The method for reducing a wrinkle according to claim 7, wherein $R_2$ represents —$SO_3H$ and the $R_3$ represents a hydrogen atom.

* * * * *

UNITED STATES PATENT AND TRADEMARK OFFICE
CERTIFICATE OF CORRECTION

Page 1 of 2

PATENT NO.         : 8,835,498 B2
APPLICATION NO.    : 13/126714
DATED              : September 16, 2014
INVENTOR(S)        : Noriko Suenobu et al.

It is certified that error appears in the above-identified patent and that said Letters Patent is hereby corrected as shown below:

Title Page,

In column 2 (page 2, item 56) at line 12, Under Other Publications, change "Folypolyglutamate" to --Folylpolyglutamate--.

In column 2 (page 2, item 56) at line 16, Under Other Publications, change "Moisturing" to --Moisturizing--.

In the Specification,

In column 3 at line 32, Change "—S—$X_1$," to -- —S—S—$X_1$,--.

In column 6 at line 41, After "—S—$X_2$," insert -- —SO—$X_3$,--.

In column 7 at line 7, Change "FIG." to --FIGS.--.

In column 7 at line 9, Change "FIG." to --FIGS.--.

In column 7 at line 11, Change "FIG." to --FIGS.--.

In column 7 at line 13, Change "FIG." to --FIGS.--.

In column 8 at line 18, Change "apyridyl" to --a pyridyl--.

In column 8 at line 19, Change "abiphenyl" to --a biphenyl--.

In column 8 at line 37, Change "chiorophenyl" to --chlorophenyl--.

In column 15 at line 38, Change "ethoxycarbonylobenzoyl" to --ethoxycarbonylbenzoyl--.

In column 21 at line 26, Change "icebath." to --ice bath.--.

In column 23 at line 30, Change "icebath." to --ice bath.--.

In column 24 at line 28, Change "ibota" to --ibotta--.

In column 25 at line 28 (approx.), Change "laked;" to --leaked;--.

In column 25 at line 58, Change "byway" to --by way--.

Signed and Sealed this
Second Day of June, 2015

Michelle K. Lee
*Director of the United States Patent and Trademark Office*

CERTIFICATE OF CORRECTION (continued)
U.S. Pat. No. 8,835,498 B2

In the Claims,

In column 28 at line 22, In Claim 1, change "toluoyl" to --toluyl--.

In column 28 at line 59 (approx.), In Claim 4, change "toluoyl" to --toluyl--.

In column 29 at line 14, In Claim 5, change "toluoyl" to --toluyl--.

In column 30 at line 1, In Claim 7, after "—SH," insert -- —$SO_3H$, —S—S—$X_1$, —S—$X_2$, —SO—$X_3$,--.

In column 30 at line 12, In Claim 7, change "toluoyl" to --toluyl--.